(12) United States Patent
Tangutoori et al.

(10) Patent No.: US 10,111,871 B2
(45) Date of Patent: Oct. 30, 2018

(54) NANOPARTICLE DRUG DELIVERY SYSTEM AND METHOD OF TREATING CANCER AND NEUROTRAUMA

(71) Applicant: Northeastern University, Boston, MA (US)

(72) Inventors: Shifalika Tangutoori, Malden, MA (US); Srinivas Sridhar, Newton, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 14/914,932

(22) PCT Filed: Aug. 27, 2014

(86) PCT No.: PCT/US2014/053006
§ 371 (c)(1),
(2) Date: Feb. 26, 2016

(87) PCT Pub. No.: WO2015/031536
PCT Pub. Date: Mar. 5, 2015

(65) Prior Publication Data
US 2016/0206615 A1 Jul. 21, 2016

Related U.S. Application Data

(60) Provisional application No. 61/870,258, filed on Aug. 27, 2013.

(51) Int. Cl.
| | | |
|---|---|---|
| *A61K 9/127* | (2006.01) | |
| *A61K 31/502* | (2006.01) | |
| *A61K 45/06* | (2006.01) | |
| *A61K 31/4188* | (2006.01) | |
| *A61K 31/5025* | (2006.01) | |
| *A61K 31/704* | (2006.01) | |
| *A61K 31/7068* | (2006.01) | |
| *A61K 33/24* | (2006.01) | |

(52) U.S. Cl.
CPC .......... *A61K 31/502* (2013.01); *A61K 9/1272* (2013.01); *A61K 31/4188* (2013.01); *A61K 31/5025* (2013.01); *A61K 31/704* (2013.01); *A61K 31/7068* (2013.01); *A61K 33/24* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,013,556 A | * | 5/1991 | Woodle | A61K 9/1271 264/4.3 |
| 6,056,938 A | | 5/2000 | Unger et al. | |
| 6,635,642 B1 | * | 10/2003 | Jackson | A61K 31/4725 514/247 |
| 8,609,088 B2 | | 12/2013 | Wolf et al. | |
| 2002/0025313 A1 | | 2/2002 | Micklus et al. | |
| 2003/0180950 A1 | * | 9/2003 | Smyth Templeton | A61K 9/1271 435/458 |
| 2009/0220587 A1 | | 9/2009 | Allon et al. | |
| 2010/0104629 A1 | * | 4/2010 | Dande | C07D 213/74 514/1.1 |
| 2010/0129456 A1 | | 5/2010 | Ishihara et al. | |
| 2011/0027171 A1 | * | 2/2011 | Stavroula | A61K 9/1271 424/1.21 |
| 2011/0123451 A1 | | 5/2011 | Kullberg | |
| 2011/0233079 A1 | * | 9/2011 | Macinnes | A61M 25/002 206/232 |

FOREIGN PATENT DOCUMENTS

| | | |
|---|---|---|
| EP | 0440289 B1 | 12/1995 |
| JP | 2001-026544 A | 1/2001 |
| KR | 10-2009-0013848 A | 2/2009 |
| WO | 91/00289 A2 | 1/1991 |
| WO | 94/05624 A1 | 3/1994 |
| WO | 2006/076681 A2 | 7/2006 |
| WO | 2008/095004 A2 | 8/2008 |
| WO | 2009/096487 A1 | 8/2009 |
| WO | 2009/129387 A2 | 10/2009 |

(Continued)

OTHER PUBLICATIONS

Blanco, et al., "Chapter 9: Targeted Nanoparticles for Cancer Therapy", Recent Advances in Novel Drug Carrier Systems, Oct. 31, 2012, pp. 241-278, retrieved from the Internet: <www.intechopen.com/books/recent-advances-in-novel-drug-carrier-systems/targeted-nanoparticles-for-cancer-therapy> on Jan. 15, 2015.

Tutt, et al., "Oral poly(ADP-ribose) polymerase inhibitor olaparib in patients with BRCA1 or BRCA2 mutations and advanced breast cancer: a proof-of-concept trial", Lancet, Jul. 24, 2010, vol. 376, pp. 235-244.

Senra, et al, "Inhibition of PARP-1 by Olaparib (AZD2281) Increases the Radiosensitivity of a Lung Tumor Xenograft", Molecular cancer therapeutics, (2011), vol. 10, pp. 1949-1958.

Miura, et al., "The combination of olaparib and camptothecin for effective radiosensitization", Radiation Oncology, (2012), vol. 7, No. 62, 9 pgs.

(Continued)

*Primary Examiner* — Jessica Worsham
(74) *Attorney, Agent, or Firm* — Posternak Blankstein & Lund LLP

(57) ABSTRACT

The invention provides pharmaceutical formulations of inhibitors for poly (ADP-ribose) polymerase (PARP) enzyme. The formulations can be used in the treatment and prevention of cancer as well as the treatment of neurotrauma and neurodegenerative diseases. The PARP inhibitor is delivered in the form of nanoparticles that provide efficient delivery of the inhibitor into cancer cells or other cells and release of the inhibitor within the cells. In treating cancer, the result is killing of tumor cells, whereas in treatment of neurotrauma and neurodegenerative disease, the result is preservation of cell function.

18 Claims, 20 Drawing Sheets

(56) References Cited

FOREIGN PATENT DOCUMENTS

| WO | 2011/097602 A1 | 8/2011 |
|---|---|---|
| WO | 2012/031205 A2 | 3/2012 |

OTHER PUBLICATIONS

Han, et al., "Targeted Radiosensitization of ETS Fusion-Positive Prostate Cancer Through PARP1 Inhibition", Neoplasia, (2013), vol. 15, No. 10, pp. 1207-1217.

Barreto-Andrade, et al., "Response of Human Prostate Cancer Cells and Tumors to Combining PARP Inhibition with Ionizing Radiation", Molecular Cancer Therapeutics, Jul. 2011, vol. 10, No. 7, pp. 1185-1193.

"Olaparib shows promise in multiple tumor types", Cancer discovery, (2013), vol. 3, Issue 7, 2 pgs.

Staropoli, et al., "Pegylated liposomal doxorubicin in the management of ovarian cancer: A systematic review and metaanalysis of randomized trials", Cancer Biology & Therapy, Jun. 2014, vol. 15, No. 6, pp. 707-720.

Chatterjee, et al., "PARP Inhibition Sensitizes to Low Dose-Rate Radiation TMPRSS2-ERG Fusion Gene-Expressing and PTEN-Deficient Prostate Cancer Cells", PloS One, Apr. 2013, vol. 8, Issue 4, 12 pgs.

Campbell, et al., "Cationic Charge Determines the Distribution of Liposomes Between the Vascular and Extravascular Compartments of Tumors", Cancer research, Dec. 1, 2002, vol. 62, pp. 6831-6836.

Lee, et al., "Combining PARP-1 Inhibition and Radiation in Ewing Sarcoma Results in Lethal DNA Damage", Molecular Cancer Therapeutics, Nov. 2013, vol. 12, No. 11, pp. 2591-2600.

Casey, et al., "Poly(adenosine diphosphate ribose) polymerase inhibition modulates spinal cord dysfunction after thoracoabdominal aortic ischemia-reperfusion", Journal of Vascular Surgery, Jan. 2005, vol. 41, No. 1, pp. 99-107.

Lang-Lazdunski, et al., "Spinal cord ischemia: Development of a model in the mouse", Stroke, Jan. 2000, vol. 31, pp. 208-213.

Lou et al., "On PAR with PARP: cellular stress signaling through poly(ADP-ribose) and PARP-1", Genes & Development, (2012), vol. 26, pp. 417-432.

Besson, "Drug targets for traumatic brain injury from poly(ADP-ribose)polymerase pathway modulation", British Journal of Pharmacology, (2009), vol. 157, pp. 695-704.

Audeh, et al., "Oral poly(ADP-ribose) polymerase inhibitor olaparib in patients with BRCA1 or BRCA2 mutations and recurrent ovarian cancer: a proof-of-concept trial", Lancet, Jul. 24, 2010, vol. 376, pp. 245-251.

Gelmon, et al., "Olaparib in patients with recurrent high-grade serous or poorly differentiated ovarian carcinoma or triple-negative breast cancer: a phase 2, multicentre, open-label, non-randomised study", The Lancet Oncology, Sep. 2011, vol. 12, , pp. 852-861.

Bundred, et al., "Evaluation of the pharmacodynamics and pharmacokinetics of the PARP inhibitor olaparib: a Phase I multicentre trial in patients scheduled for elective breast cancer surgery", Investigational New Drugs, (2013) vol. 31, pp. 949-958.

Riganti, et al, "Liposome-Encapsulated Doxorubicin Reverses Drug Resistance by Inhibiting P-Glycoprotein in Human Cancer Cells", Molecular Pharmaceutics, (2011), vol. 8, pp. 683-700.

Stone, et al, "PJ34, a poly-ADP-ribose polymerase inhibitor, modulates renal injury after thoracic aortic ischemia/reperfusion", Surgery, Aug. 2005, vol. 138, No. 2, pp. 368-374.

* cited by examiner

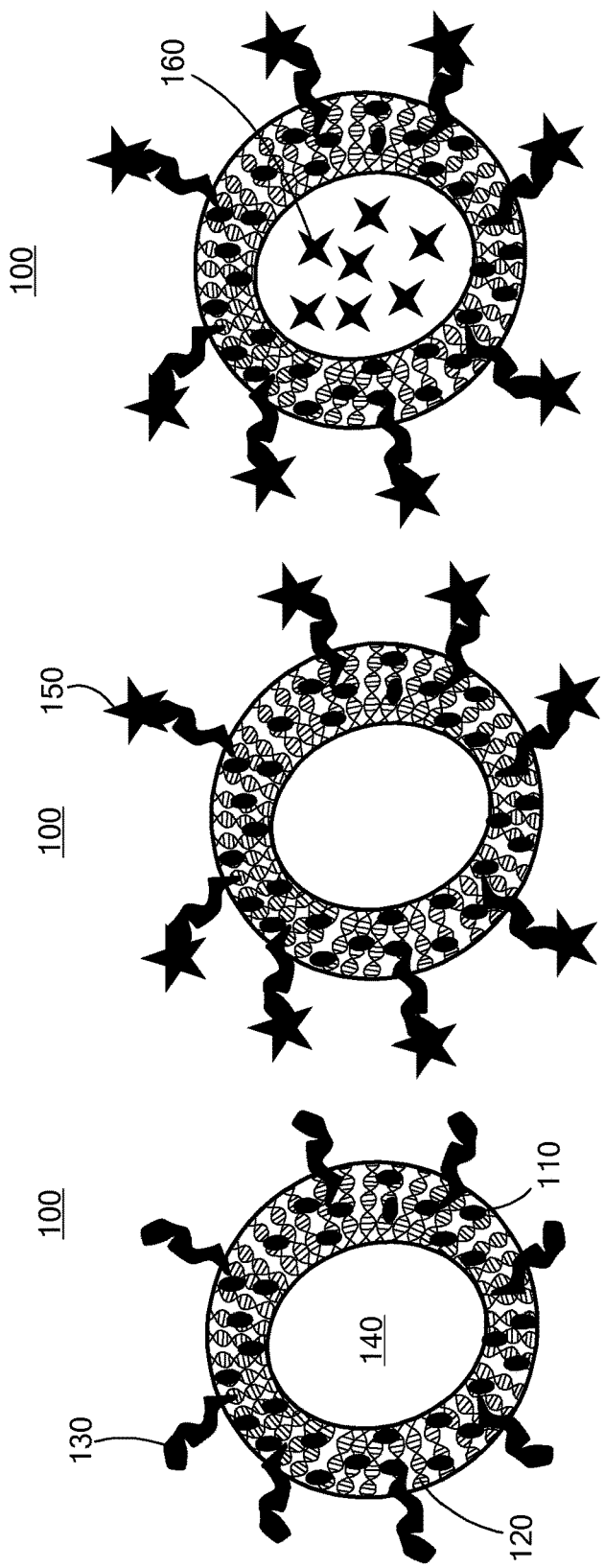

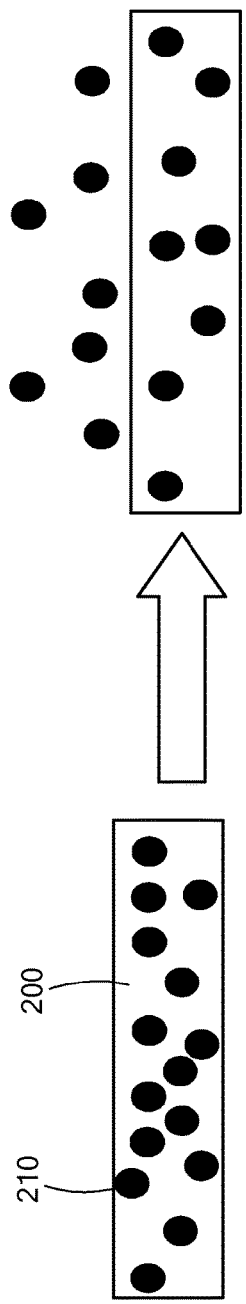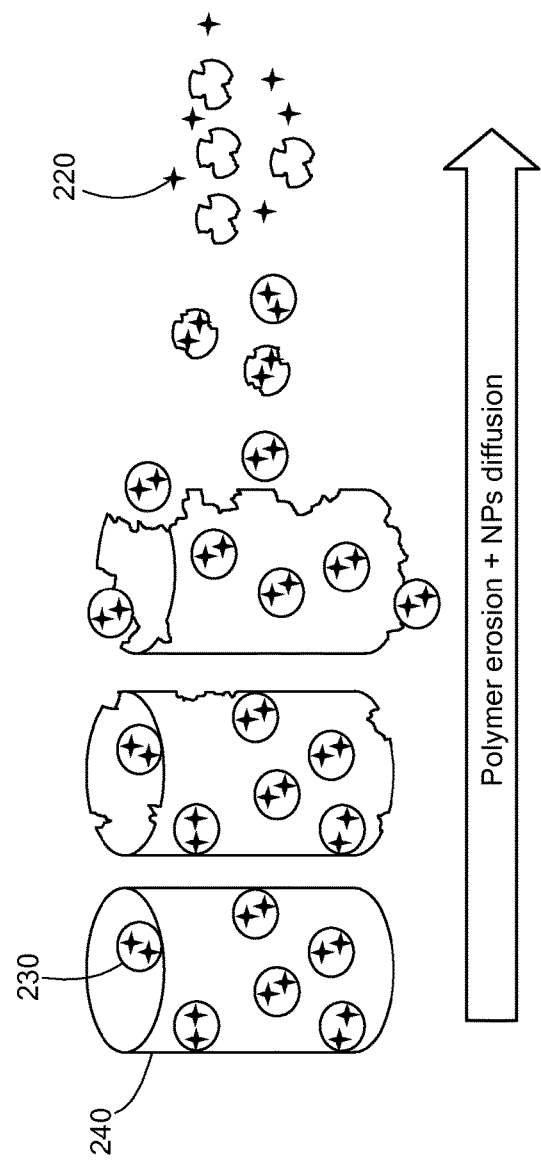
FIG. 2A
FIG. 2B

NANOPARTICLE DRUG DELIVERY SYSTEM AND METHOD OF TREATING CANCER AND NEUROTRAUMA

CROSS REFERENCE TO RELATED APPLICATIONS

This application claims the priority of U.S. Provisional Application No. 61/870,258 filed 27 Aug. 2013 and entitled "Nanoplatforms for Delivery of Inhibitors and Biologics", the whole of which is hereby incorporated by reference.

BACKGROUND

Defective DNA damage repair pathways and gene mutations in transcriptional pathways have been established as predominant targets for poly (ADP-ribose) polymerase (PARP) inhibition therapy in a wide spectrum of cancers (1-4). PARP-1, a nuclear enzyme, plays a crucial role in the DNA repair pathways in a cell, rendering it the 'Achilles Heel' in cancer therapy. PARP inhibitor therapy is particularly effective through a synthetic lethality mechanism in tumors where genetic mutations, such as BRCA for breast and ovarian cancer and PTEN for prostate cancers, lead to defects in the DNA repair pathways (4,15). Olaparib is an orally active PARP inhibitor, which competitively binds to the NAD$^+$ binding site of PARP, thus attenuating the single strand DNA repairing mechanisms intervened by PARP (5-7). Olaparib and other PARP inhibitors are well established radiosensitizers as they effectively sensitize various cancers to radiation therapy by inhibiting the PARP activation due to DNA damage thus enhancing the tumor destruction in several cancers (8,9), especially in prostate cancers (10-13).

Presentation of castration-resistant prostate cancer (CRPC) is a major cause for fatalities in prostate cancer patient cohorts, either as localized or metastasized cancer (mCRPC) (20-22). Several studies have postulated and derived the synthetic lethality associated with PARP-1 inhibition and PTEN deficiency in prostate cancers (23), which is similar to BRCA mutations in breast and ovarian cancers (7,24). PARP-1 inhibition also has therapeutic implications specifically in the CRPC models of prostate cancer, where it appears to have cross talks with ligand independent aberrant androgen receptor (AR) activity, rendering the cancer insensitive to androgen depletion therapy (25). In addition, PARP-1 is also involved in the AR sensitive cancers where it is enzymatically linked to AR activity and progression of cancer (25). Specific gene fusions (TMPRSS2:ERG fusions) (26) and chromosomal rearrangements including PTEN and TP53 mutations are frequently detected in prostate cancers that are prone to become castration resistant (27-29).

Olaparib is currently being tested via oral administration in several clinical trials for a variety of cancers including prostate, pancreatic (14), breast (4,15) and ovarian cancers (4). The current treatment regimen followed in clinical trials with Olaparib includes p.o. administration at 400 mg b.i.d (3,4). Although promising, the pharmacokinetic profile derived from several clinical trials suggests that the oral treatment regimen with olaparib faces the following limitations: 1) The patient is required to follow a cumbersome routine of swallowing 16 capsules every day. 2) No dose dependent accumulation has been observed at the tumor site (15). 3) Olaparib is rapidly eliminated from the circulation in about 6 to 7 hrs and has poor bioavailability due to first pass metabolism into non-therapeutic metabolites. These limitations indicate that there is a compelling need for alternative delivery methods for olaparib and other PARP inhibitors.

SUMMARY OF THE INVENTION

The invention provides various formulations of PARP inhibitors for use in the treatment and prevention of cancer as well as the treatment of neurotrauma, and neurodegenerative diseases. Many of the formulations utilize packaging of a PARP inhibitor into nanoparticles that provide efficient delivery of the inhibitor into cancer cells or other cells and release of the inhibitor within the cells. Formulations of PARP inhibitors according to the invention can effectively kill tumor cells and shrink tumors. Surprisingly, the formulations are also effective at treating and promoting recovery from neurotrama and neurodegenerative diseases.

One aspect of the invention is a nanoparticulate formulation of an inhibitor of a poly (ADP-ribose) polymerase (PARP) enzyme. The formulation includes a suspension of lipid vesicles (liposomes) in an aqueous medium. The lipid vesicles have a positive surface charge as a result of including positively charged lipids. The lipid vesicles have an average diameter in the range from about 50 nm to about 200 nm, and preferably in the range of about 80 nm to about 120 nm, or about 80 nm to about 100 nm, or about 100 nm. The lipid vesicles contain a PARP inhibitor, and also include a PEGylated lipid moiety.

Another aspect of the invention is a sustained release formulation of a PARP inhibitor. The formulation contains a PARP inhibitor embedded in a matrix, and the matrix includes or is formed by a biodegradable polymer. In some embodiments, the sustained release formulation contains a plurality of lipid vesicles embedded in the matrix. The lipid vesicles have a positive surface charge, have an average diameter in the range from about 50 nm to about 200 nm, contain a PARP inhibitor, and include a PEGylated lipid moiety.

Still another aspect of the invention is a method of treating cancer. The method includes the step of administering a PARP inhibitor formulation as described above to a subject in need thereof.

Yet another aspect of the invention is a method of treating neurotrauma or a neurodegenerative disease or condition. The method includes the step of administering a PARP inhibitor to a subject in need thereof. In some embodiments of the method, the PARP inhibitor is administered as a formulation as described above.

Another aspect of the invention is a method of preparing a nanoparticulate PARP inhibitor formulation. The method includes the steps of: (a) providing a mixture containing a zwitterionic phospholipid, a cationic lipid, cholesterol, a PEGylated lipid, and a PARP inhibitor dissolved in organic solvent; (b) preparing a dry lipid film by removing the solvent from said mixture; (c) hydrating the lipid film with an aqueous solution to form a suspension of hydrated lipid structures containing the PARP inhibitor; (d) sonicating the suspension; and (e) passing the sonicated suspension through a nanoporous membrane to yield the nanoparticulate PARP inhibitor formulation.

The invention further includes a kit containing a PARP inhibitor formulation as described above, packaging materials, and instructions for performing any of the methods of treatment as described above.

BRIEF DESCRIPTION OF THE DRAWINGS

FIGS. 1A-1C are schematic representations of three different embodiments of nanoparticles of nanoparticulate formulations of a PARP inhibitor according to the invention. In FIG. 1A an embodiment is depicted which lacks a targeting moiety and contains a PARP inhibitor within the lipid bilayer phase of the nanoparticle. In FIG. 1B an embodiment is shown that includes a targeting moiety and a PARP inhibitor in the lipid bilayer phase. In FIG. 1C an embodiment is shown that has a targeting moiety, a PARP inhibitor in the lipid bilayer phase, and also another pharmaceutical agent in the aqueous phase in the lumen of the nanoparticle.

FIG. 2A is a schematic representation of an implantable PARP inhibitor delivery device with a single release mechanism. The device contains a PARP inhibitor embedded in a biodegradable matrix. FIG. 2B is schematic representation of an implantable PARP inhibitor delivery device with a dual release mechanism. The Jo device contains a nanoparticle such as shown in any of FIGS. 1A-1C embedded in a biodegradable matrix.

FIG. 6B is a graph showing quantification of cleaved PARP per nucleus. LNCaP cells were treated as described for FIG. 6A except that a separate control sample was not irradiated. The symbol  indicates a statistically significant difference between the signal from the NanoOlaparib 2Gy sample and the signal from the olaparib 2Gy sample, with $p<0.01$. Statistically significant differences are represented as .

Signals from DAPI staining of individual cells were quantified.

DETAILED DESCRIPTION OF THE INVENTION

Figure 3A:
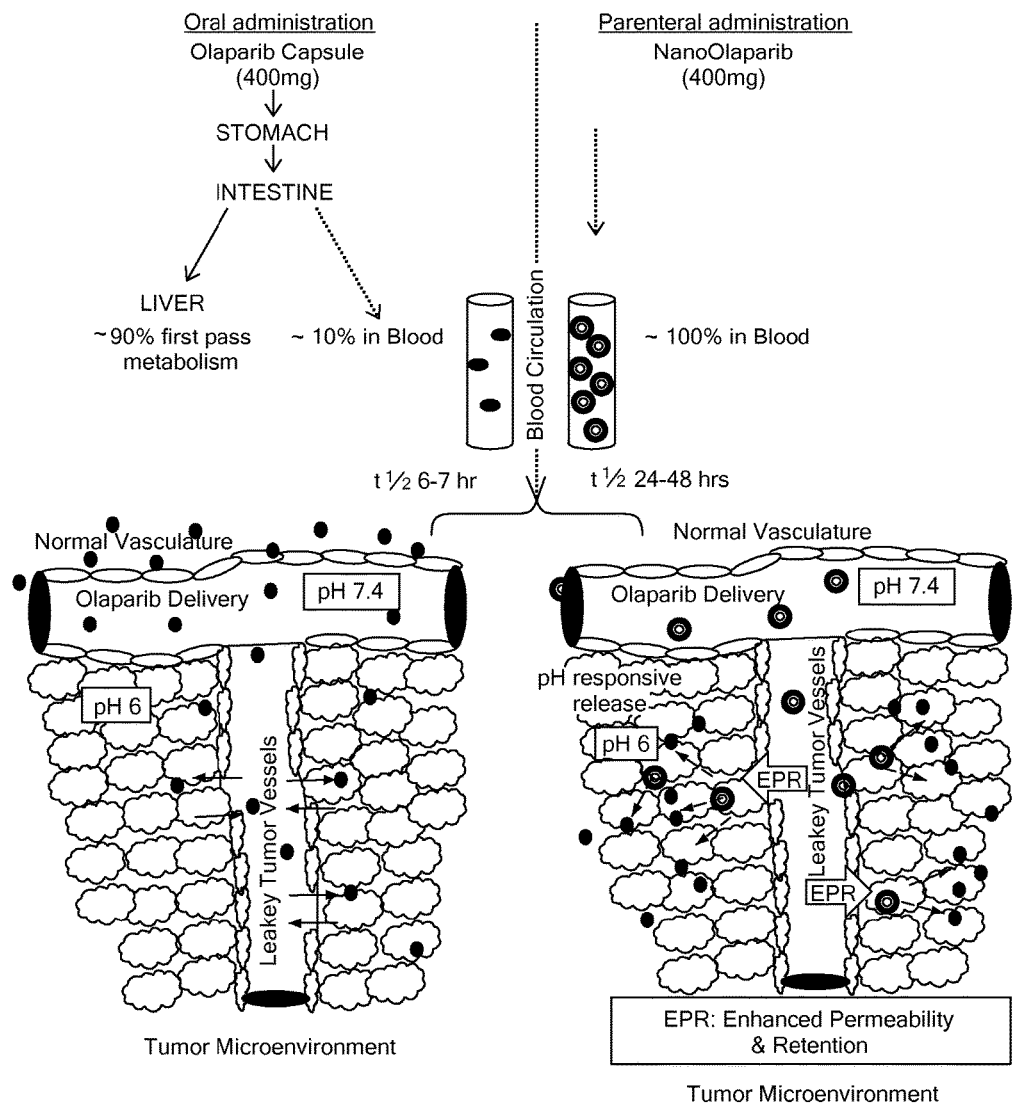
FIG. 3A is a schematic representation of processes of PARP inhibitor delivery to a tumor by oral administration vs. perenteral administration of a nanoparticulate formulation of the invention.

The inventors have developed a variety of novel formulations of PARP inhibitors and other drugs or biologics that unexpectedly promote the delivery of highly effective therapeutic concentrations of the inhibitors and other substances to their target in the human or animal body. These formulations can be used in the treatment and prevention of cancer as well as the treatment of neurotrauma, and neurodegenerative diseases. PARP inhibitors are particularly difficult to administer and deliver because of their strongly hydrophobic nature. Formulations of the invention package PARP inhibitors and other compounds into lipid-containing nanoparticles that provide efficient delivery to intracellular targets, such as PARP. The nanoparticles have the capability to cross the blood-brain barrier, and therefore can be used for treatment of neurological diseases and conditions affecting the brain. After being taken up by cells, the nanoparticles release the inhibitor or other substance within the cells. Formulations of PARP inhibitors according to the invention can effectively kill tumor cells and shrink tumors. The PARP inhibitor formulation of the invention are also remarkably effective at treating and promoting recovery from neurotrama and neurodegenerative diseases.

The nanoparticulate formulations of the invention are aqueous suspensions of lipid-based nanoparticles which contain a PARP inhibitor or other inhibitor or biologic agent. In the case of PARP inhibitors, and other agents which are highly hydrophobic, the inhibitor agent is integrated entirely or at least in part in the lipid portion of the nanoparticle. While not intending to limit the invention to any particular configuration, the lipid is believed to be in the form of a bilayer membrane forming a spherical structure such as a liposome or lipid vesicle. An important feature of the invention is the packaging of sufficiently large amounts of the PARP inhibitor or other agent such that a significant therapeutic effect is achieved upon delivery. The lipid vesicles are preferably small and unilamellar, having an average size (diameter) in the range from about 50 nm to 200 nm, preferably 80 nm to 120 nm, 80 nm to 100 nm, or about 100 nm. So as to promote survival in the bloodstream, the lipid vesicles have polyethylene glycol (PEG) groups exposed on their outer surfaces. The lipid vesicles also bear a net positive surface charge, preferably in the range of +15 mV to +40 mV, through the inclusion of one or more types of lipid that are positively charged at physiological pH of the blood or extracellular medium (e.g., pH 7.4), such as N-[1-(2,3-dioleoyloxy)propyl]-N,N,N-trimethylammonium methylsulfate (DOTAP). For other examples of cationic lipids, see WO 2009129387, WO9405624, and U.S. Pat. No. 6,056,938. Positive surface charge promotes the uptake of the vesicles into cells. In general, suitable lipid vesicles can be formed from one or more zwitterionic phospholipids (e.g., phosphatidylcholine (PC) and/or phosphtatidyletha-nolamine (PE)), one or more positively-charged lipids, and cholesterol. PEG groups can be introduced by covalent attachment to the polar head groups of one or more types of phospholipid (e.g., PEGylated PE). An example of a suitable PEGylated phospholipid is 1,2-distearoyl-sn-glycero-3-phosphoethanolamine-N-[amino(polyethyleneglycol)] (DSPE-PEG). PEG moieties having different molecular weights can be employed, such as PEG2000 for example.

A variety of different lipid compositions can be used to make suitable lipid vesicles for the nanoparticulate formulations. The vesicles can contain dipalmitoylphosphatidyl-choline (DPPC) and cholesterol, such as in a DPPC:cholesterol molar ratio from about 1 to 7 moles DPPC to about 1 to 4 moles cholesterol. The vesicles also can contain or consist essentially of DPPC, DOTAP, cholesterol, and DSPE-PEG2000. The molar ratio of DPPC, DOTAP, cholesterol, and DSPE-PEG2000 can be, for example, about 1 to 8 moles DPPC to about 0.05 to 1 mole DOTAP to about 0.5 to 2 moles cholesterol to about 0.1 to 5 moles DSPE-PEG2000. When the vesicles are loaded with olaparib, suitable vesicles can include a molar ratio of DPPC, DOTAP, cholesterol, and DSPE-PEG2000 of about 5.4 moles DPPC to about 0.25 moles DOTAP to about 0.78 moles cholesterol to about 0.14 moles DSPE-PEG2000, for example. When the inhibitor is BMN-673, the molar ratio of DPPC, DOTAP, cholesterol, and DSPE-PEG2000 can be about 1.4 moles DPPC to about 0.09 moles DOTAP to about 0.78 moles cholesterol to about 0.11 moles DSPE-PEG2000, for example.

The nanoparticles (the terms "nanoparticles", "liposomes", and "lipid vesicles" are used interchangeably herein) can be made by any of a variety of methods known in the art. A preferred method involves first forming a dry lipid film by combining the desired lipids in organic solvent solution (e.g., chloroform or a chloroform/methanol mixture), addition to the solvent of a PARP inhibitor or other hydrophobic agent in solvent solution, and thorough drying of the combined lipid-inhibitor mix by solvent evaporation. The dried lipid-inhibitor film is then hydrated in the presence of a suitable aqueous medium, preferably one that is selected to be the internal aqueous medium of the vesicles (e.g., phosphate-buffered saline). The aqueous medium also can contain one or more additional, water-soluble pharmacological or biological agents. The hydrated lipid-inhibitor material is formed into crude vesicles by sonication, and the crude vesicles are then homogenized and sized by repeated passage through a nanoporous membrane. Such membranes are commercially available in a wide variety of materials (e.g., inorganic materials such as alumina or silica and organic materials such as polycarbonate) and pore sizes (100 nm preferred). After formation and sizing of the vesicles, their size and composition can be determined by light scattering or electron microscopy, and if desired the external solution can be exchanged by conventional methods, such as size exclusion chromatography.

The nanoparticles of the invention allow the packaging of sufficiently large amounts of the PARP inhibitor or other agent so that a significant therapeutic effect is achieved upon delivery. This is achieved at least in part by loading the lipid phase of the nanoparticles with the PARP inhibitor or other hydrophobic active agent. Because the agent is not present entirely free in solution, but is entirely or at least in part bound in the lipid, it can be useful to determine an effective concentration of the agent in the nanoparticles. The effective concentration is the concentration that would be obtained, based on the known amount of agent per nanoparticle divided by the known volume of the nanoparticle, if the entire amount of the agent were free. The effective concentration can be used to optimize delivery and therapeutic effect of the agent using the nanoparticles. For example, the inventors have determined that the olaparib is therapeutically active at an effective concentration in the range from about 400 µM to about 20 mM, whereas BMN-673 is active at an effective concentration from about 50 nM to about 1 µM.

In certain embodiments the nanoparticles include a targeting moiety, which is a molecule exposed on the outer surface of the nanoparticles that binds to a selected target cell, such as a tumor cell or a cell of the central nervous system. The targeting moiety may be an antibody, antibody fragment, oligonucleotide, peptide, hormone, ligand, cytokine, peptidomimetic, protein, carbohydrate, chemically modified protein, chemically modified nucleic acid, or chemically modified carbohydrate that targets a known cell-surface protein (see, for example, US2011/0123451). The targeting moiety may be derived from a molecule known to bind to a cell-surface receptor. For example, the targeting moiety may be derived from low density lipoproteins, transferrin, EGF, insulin, PDGF, fibrinolytic enzymes, anti-HER2, annexins, interleukins, interferons, erythropoietins, or colony-stimulating factor. The targeting moiety may be an antibody or antibody fragment that targets liposomes to the blood-brain barrier, for example, an antibody or antibody fragment to transferrin receptor, insulin receptor, IGF-I or IGF-2 receptor (see, for example, US 2002/0025313).

The targeting moiety may be attached to a phospholipid or PEG moiety in the nanoparticle by a linker. Linkers for coupling peptides, proteins, and other molecules to phospholipids in liposomes are known in the art (see, for example, WO 1991000289, US20090220587, and WO 2008095004). The linker may be a maleimide-containing compound, for example, N-succinimidyl 3-(2-pyridyldithio) propionate (SPDP), N-succinimidyl 4-(p-maleimidophenyl) butyrate (SMPB), N-succinimidyl 3-maleimidobenzoate (SMB), N-succinimidyl 3-maleimidibutyrate (GMBS), N-succinimidyl 6-maleimidocaproate (EMCS), N-succinimidyl 3-maleimidopropionate, N-succinimidyl trans-4-(N-maleimidylmethyl) cyclohexane-1-carboxylate (SMCC) or N-succinimidyl maleimidylacetate (AMAS).

Some representative embodiments of nanoparticles of the invention are shown in FIGS. 1A-1C. FIG. 1A shows nanoparticle 100 that contains active agent 110, such as a PARP inhibitor, within lipid bilayer phase 120 of the nanoparticle. PEG moiety 130 is attached to the outer surface of the bilayer membrane. The core of the nanoparticle (lumen of the lipid vesicle) is buffer solution 140. This embodiment lacks a targeting moiety. In FIG. 1B an embodiment is shown that is similar to the embodiment of FIG. 1A but also includes targeting moiety 150. In the embodiment of FIG. 1C, an additional, water-soluble, active agent 160 is added to the aqueous phase in the lumen.

The formulations of the invention can utilize either a single component release mechanism or a two-component release mechanism. FIG. 2A shows an implantable delivery device having a single release mechanism. Implant 200 is coated with the active form of drug 210, which diffuses away from the implant after implantation. Alternatively, drug 210 could be embedded in a biodegradable matrix, which releases the drug as it decomposes. FIG. 2B shows an implantable delivery device with a dual release mechanism. Drug 220 is packaged in nanoparticle 230, which in turn is embedded in a biocompatible matrix which forms the body of implant 240. The matrix can be made of or contain, for example, PLGA, chitosan, or another biodegradable polymer. In the first release step, the matrix slowly becomes degraded, and the nanoparticles diffuse away. In the second release step, the nanoparticles are degraded (e.g., after cellular uptake), and the active form of the drug is released.

Figure 3B:
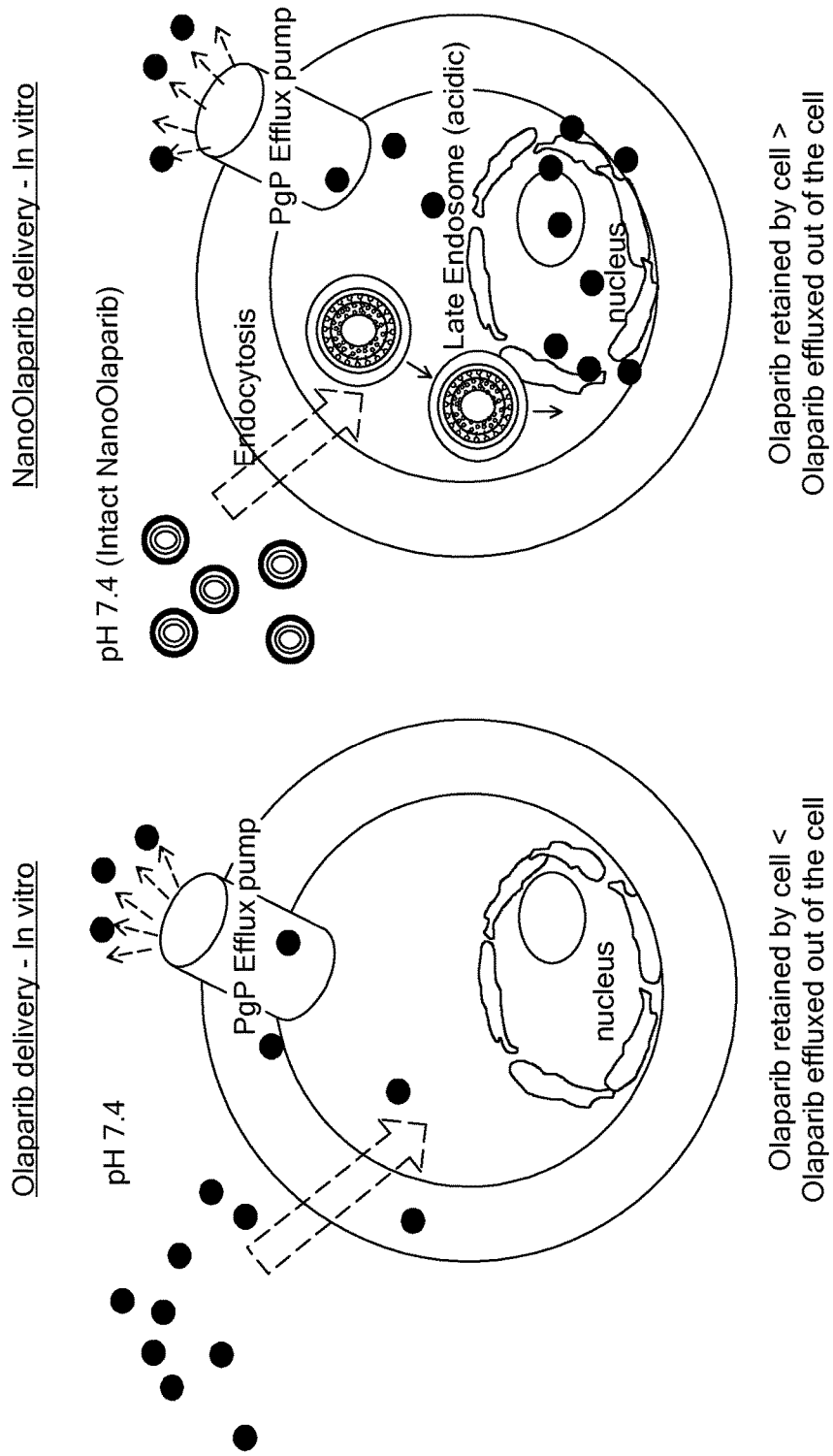
FIG. 3B is a schematic representation comparing the cellular uptake of free PARP inhibitor vs. nanoparticulate PARP inhibitor.

The nanoparticulate carriers of the invention are capable of overcoming barriers otherwise encountered in vivo to the delivery of a PARP inhibitor such as olaparib to a tumor. A possible mechanism is depicted in FIG. 3B. The fate of olaparib delivered orally in capsule form is shown on the left. Free olaparib traverses vessel walls non-specifically, leading to low bioavailability after first-pass metabolism. The fate of olaparib delivered in parenteral injections as the nanoparticulate formulation (NanoOlaparib) is shown on the right. NanoOlaparib particles accumulate in the tumor due to the EPR effect caused by leaky tumor vasculature and the size of the particles, and the acidic microenvironment of the tumor releases free olaparib from the particles, resulting in ~100% bioavailability. FIG. 3B is a schematic comparing the cellular uptake of free olaparib and NanoOlaparib by cells in the in vitro settings where the entire drug added is available for cellular uptake. The net intracellular concentration of NanoOlaparib is believed to be higher than that of olaparib due to higher uptake and evasion of PgP mediated drug efflux.

Nanoparticulate formulations of the invention can be loaded with any hydrophobic active agent, including the PARP inhibitor compounds of Table 1.

| PARP Inhibitor | Compound Name |
|---|---|
| Olaparib (AZD2281, Ku-0059436) | 4-(3-(1-(cyclopropanecarbonyl) piperazine-4-carbonyl)-4-fluorobenzyl)phthalazin-1(2H)-one |
| Veliparib (ABT-888) | (R}-2-(2-methytpynolidin-2-yl)-1 H-benzo[d]imidazole-4-carboxamide |
| Rucaparib (AG-014699) (PF-01367338) | 6-ftuoro-5-(4-((methytamino) methyl)phenyl}-3,4-dihydro-2H-azepino[5,4,3-cd] indol~1(6H}-one phosphoric acid |
| Iniparib (851•201) | 4-iodo-3-nitrobenzamide |
| BMN 673 | 3H-pyrido[4,3,2-de]phthalazin-3-one, 5-fluoro-8-(4-fluorophenyl)-2,7,8,9-tetrahydro-9-(1-methyl-1H-1, 2,4-triazo~5-yl)-,(8S,9R)- |
| 3-Aminobenzamide | 3-Aminobenzamide |
| ME0328 | 3,4-dihydro-4-oxo-3,4-dihydro-4-oxo-N-[(1S)-1-phenytethyl]-2-qulnazolinepropanamide |
| PJ34 HCl | acetamide, N-(5,6-dihydro-6-oxo-2-phenarthridinyl)-2-{dimethylamino)-, hydrochloride (1:1) |
| AG-14361 | imidazo[4,5,1-jk][1,4]benzodiazepin-7(4H)-one,2-[4-[(dlmethylamino) methyl]phenyl]-5,6-dihydro- |
| INO-1001 | 3-aminobenzamide |
| UPF 1069 | 1(2H)-isoquinolinone, 5-(2-oxo-2-phenytethoxy)- |
| AZD2461 | 1(2H)-phthalazinone,4-[[4-fluoro-3-[(4-methoxy-1-piperidinyl) carbonyl]phenyl]methyl]- |
| A-966492 | 2-(2-fluoro-4-((S)-pyrrolidin-2-yl) phenyl)-3H-benzo[d]imidazole-4-carboxamide |

The nanoparticulate formulations can further include a second active agent, such as an anticancer agent such as cisplatin, temozolomide, gemcitabine, doxorubicin, a PI3K inhibitor, a MEK inhibitor, an ATM inhibitor, or another anti-cancer agent. The second active agent can be loaded either into the lipid bilayer phase or into the aqueous compartment within the particle lumen.

The formulations can be prepared for any type of parenteral administration, including intravenous administration, as is generally known. They also may be prepared in a manner suitable for intranasal administration. Methods of preparing formulations for intranasal delivery of liposomal particles are known in the art (see, for example, EP 0440289). The formulation may be prepared in a manner suitable for intranasal delivery to the central nervous system according to known methods (see, for example, U.S. Pat. No. 8,609,088). Sustained release preparations are preferably injected intramuscularly, intracranially, or into a tumor.

The invention includes methods of preparing a nanoparticulate PARP inhibitor formulation. The method includes providing a mixture containing a zwitterionic phospholipid, a cationic lipid, cholesterol, a PEGylated lipid, and a PARP inhibitor dissolved in an organic solvent. The solvent may contain chloroform, methanol, hexane, or another organic solvent, or a mixture thereof. For examples of cationic lipids, see WO 2009129387, WO9405624, U.S. Pat. No. 6,056,938. A dry lipid film is prepared by removing the organic solvent from the mixture. In one embodiment of the method, the organic solvent is removed by evaporation.

A suspension of hydrated lipid structures containing the PARP inhibitor is formed by hydrating the lipid film with an aqueous solution. In one embodiment, the aqueous solution is phosphate-buffered saline (PBS). In one embodiment, the hydrated lipid structures are formed by continuously mixing the suspension. In one embodiment, the hydration step is performed at 45-50° C. In one embodiment, the hydration step is performed at room temperature.

The hydrated lipid structures are reconfigured to yield a population of small homogeneous nanoparticles of the desired size. In one embodiment the nanoparticles are processed by sonication. Sonication is preferably performed at a temperature from 0-25° C., or 0-37° C. In one embodiment the nanoparticles are reconfigured and size-selected by repeated extrusion through a nanoporous membrane. In some embodiments, the extrusion is performed at a temperature from 0-25° C., or 0-37° C., or at about 37° C. In some embodiments, the extrusion involves passing the nanoparticle suspension through a porous membrane about ten times. In one embodiment, the pore size of the membrane is 200 nm. In one embodiment, the nanoparticles are size-selected by sonication followed by extrusion. In some embodiments the desired size of the nanoparticles is 80-100 nm, 80-120 nm, or 100-120 nm.

The invention also includes methods of treating cancer in a subject by administering a PARP inhibitor formulation described herein. The cancer can be, for example, prostate cancer, breast cancer, lung cancer, Ewing's sarcoma, pancreatic cancer, head and neck cancer, cervical cancer, ovarian cancer, colorectal cancer, bone cancer, brain tumor, liver cancer, lymphoma, melanoma, leukemia, neuroblastoma, nasopharyngeal cancer, anal cancer, appendix cancer, carcinoma, sarcoma, skin cancer, bile duct cancer, bladder cancer, bone cancer, brain stem glioma, brain tumor, uterine cancer, vaginal cancer, penile cancer, endometrial cancer, eye cancer, oral cancer, gallbladder cancer, stomach cancer, testicular cancer, kidney cancer, intestinal cancer, throat cancer, or thyroid cancer.

The cancer may associated with a genetic mutation. For example, the cancer may be associated with a mutation in a gene involved in DNA repair, such as BRCA1, BRCA2, ATM, NBS, MRE11, BLM, WRN, RECQ4 (RECQL4), FANCA, FANCB, FANCC, FANCDI, FANCD2, FANCE, FANCF, FANCG, FANCI, FANCJ, FANCL, FANCM, FANCN, XPC, XPE(DDB2), XPA, XPB, XPD, XPF, XPG, XPV(POLH), hMSH2, hMSH6, hMLH1, hPMS2, or MUTYH. The cancer may associated with a mutation in PTEN, TP53, TMPRSS2, ERG, EWS, or FLI. The cancer may be associated with a gene fusion, for example, TMPRSS2:ERG or EWS:FLI.

The invention further includes methods of treating neurotrauma or a neurodegenerative disease by administering a PARP inhibitor formulation described herein. For example, the neurodegenerative disease may be Alzheimer's disease, Parkinson's disease, Huntington's disease, amyotrophic lateral sclerosis (ALS), motor neuron disease, ataxia telangiectasia, autosomal dominant cerebellar ataxia, Batten disease, corticobasal degeneration, Creutzfeldt-Jakob disease, fatal familial insomnia, hereditary motor and sensory neuropathy with proximal dominance, Locomotor ataxia, Lyme disease, Machado-Joseph disease, mental retardation, multiple system atrophy, neuroacanthocytosis, Niemann-Pick disease, pontocerebellar hypoplasia, protein aggregation, pyruvate dehydrogenase deficiency, Refsum disease, Sandhoff disease, Shy-Drager syndrome, spinocerebellar ataxia, subacute combined degeneration of spinal cord, subacute sclerosing panencephalitis, tabes dorsalis, Tay-Sachs disease, toxic encephalopathy, toxic leukoencephalopathy, wobbly hedgehog syndrome, epilepsy, schizophrenia, dementia, sclerosis of the brain, impaired myelination of nerve fibers, nerve degeneration associated with diabetes, or senile degeneration of the brain. The neurotrauma may be traumatic brain injury, traumatic nerve damage, post-operative nerve damage, spinal cord injury, stroke, or cerebral ischemia.

The PARP inhibitor formulation may be administered by intravenous, intramuscular, subcutaneous, or intracranial injection. Nanoparticulate PARP inhibitor formulations of the invention release the PARP inhibitor at a pH below 7, such as at a pH of 6.8, 6.7, 6.6, 6.5, 6.4, 6.3, 6.2, 6.1, or 6.0. The formulations are capable of selective delivery of the PARP inhibitor to tumor cells following administration, such as by intravenous injection, of the formulation into a subject bearing a tumor. The nanoparticulate PARP inhibitor formulations are capable of reducing tumor mass and/or killing tumor cells when administered to a subject bearing a tumor. The subject can be a human or animal subject, such as a human patient.

The method of treating cancer, neurotrauma, or a neurodegenerative disease may also involve other forms of therapy. For example, the method may include administering a PARP inhibitor formulation described herein in conjunction with radiation therapy, non-PARP inhibiting chemotherapy, or surgery. The method may involve one or more rounds of radiation therapy and/or non-PARP inhibitor chemotherapy. The PARP inhibitor formulation described herein may be administered prior to, subsequent to, or concurrent with other forms of therapy.

The method may involve administering the PARP inhibitor formulation described herein in one or more doses.

The nanoparticulate PARP inhibitor formulations of the present invention offer the following advantages compared to the administration of free PARP inhibitor such as olaparib: 1) high biocompatibility and increased bioavailability, 2) extended Jo residence time in the plasma, 3) passive targeting to the tumor due to enhanced permeation and retention (EPR), 4) a pH-responsive release profile in the tumor microenvironment; and 5) greater and faster nuclear localization of the PARP inhibitor. These advantages are especially significant in view of the need to deliver very high clinically relevant doses of the drug in order to effectively destroy a tumor.

The invention also includes kits containing any of the PARP inhibitor formulations described herein, together with packaging materials and instructions for performing any of the methods of treatment described herein.

EXAMPLES

Example 1: Materials and Methods

Synthesis of NanoOlaparib: 1,2-dipalmitoyl-sn-glycero-3-phosphocholine (DPPC), Cholesterol, 1,2-distearoyl-sn-glycero-3 phosphoethanolamine-N-[methoxy(polyethyleneglycol)-2000(DSPE-mPEG-2000), 1,2-dioleoyl-3-trimethylammonium-propane (chloride salt) (DOTAP) were purchased from Avanti Polar Lipids (Alabaster, Ala.). Briefly, all the lipids and polymers (Avanti polar Lipids) with Olaparib, were dissolved in chloroform and the solvent was evaporated to form the lipid-polymer-Olaparib melt. The film was dried overnight under vaccum, hydrated with aqueous solvent at 50° C. to for a pre-w/o emulsion. The pre-emulsion was sonicated at room temperature for 10 min, yielding highly condensed lipid nanoparticles of Olaparib.

HPLC analysis: The concentration of Olaparib encapsulated was determined using HPLC. The mobile phase was optimized to be methanol: water (64:36) run on a reverse phase C18 column (SUPELCO™), and the Olaparib was detected at 207 nm. All the doses used in the following studies were derived from the standard curve obtained using a working range of serially diluted Olaparib solutions in mobile phases as described above. The loading efficiency across the batches was around 80-90%.

Physicochemical characterization of NanoOlaparib: The particle size was measured using ZetaPlus Particle Sizing Software Version 5.23 (Brookhaven Instruments Corp.). The stability in terms of particle size was determined after 24 hours, 5 months and 7 months of storage at 4° C. The pH dependent change in the particle size was determined at pH 7.4 and pH 6 at 0 min and 10 min after incubating the NanoOlaparib in respective buffers.

Transmission Electron Microscopy: We next examined NanoOlaparib using a Transmission electron microscopy (TEM) JEOL model JEM-1000 microscope. NanoOlaparib was formulated and the samples were diluted 50 times with PBS. Silicon monoxide formvar-coated 200 mesh grid was used for imaging. Briefly the grids were washed with drop of filtered water for 1 min and blotted dry with filter paper. A 10 μL aliquot of the sample was pipetted onto the grid for 1 min and blotted dry followed by 1% 1% uranyl acetate staining and the grid was allowed to dry at room temperature. A drop of filtered water was pipetted again and allowed to dry at room temperature. The TEM micrographs were captured using AMT camera system at an acceleration voltage of 80 kV. The magnification bar in the micrograph is 500 nm.

Release studies: The release studies were carried out based on dialysis, modified for NanoOlaparib. Briefly, a volume of 0.4 mL of NanoOlaparib diluted with 55% of either PBS or FBS was loaded into a Float-A-Lyzer® G2 (Spectrum® Laboratories, INC, Cat # G235025) with a cellulose ester membrane. The dialysis bag was suspended in 80 mL of PBS without Ca and Mg, maintained at 37±0.5° C. and was constantly rotated at 200 r.p.m using suitable size of teflon coated magnetic stir bar in the beaker. At predetermined time intervals extended over 7 days, 1 mL aliquots from the release media (in beaker) were sampled and replaced with 1 mL of fresh PBS kept at 37° C. The Olaparib concentrations in the 1 mL aliquots were quantified using HPLC, and all the experiments were done in duplicates.

In vitro characterization of NanoOlaparib: For in vitro studies we used PTEN deficient human prostate cancer cell lines PC3 (ATCC), LNCaP (ATCC) and mouse cell line FKO1. All the cells lines were maintained in the appropriate media suggested by ATCC. Briefly, a complete media was formulated by adding 10% Fetal Bovine Serum from HyClone (FBS) to F12-k (PC3), RPMI (LNCaP) and DMEM supplemented with growth factors such as Bovine Pituitary Extract, (Life Technologies cat #: 13028014), final conc. 25ug/ml, Insulin, (Sigma Aldrich Cat#:16634-50 mg), final conc. 5ug/ml, EGF (Life Technologies Cat#: PHG0311), final conc 6 ng/ml (FKO1). The FKO1 cells were grown on collagen-coated plates (VWR Cat#: 47743-656). CellTiter-Glo® luminescent cell viability reagent was ordered from Promega, CA Cat # G7570. Clonogenic assay kit was bought from BioPioneer, CA, Cat # CODE: CA-001.

Irradiation for in vitro studies: Radiation was delivered using the Small Animal Radiation Research Platform (SARRP) at DFCI, a gantry mounted x-ray tube and flat panel imager capable of fixed field irradiation, rotation therapy and cone-beam CT (CBCT) imaging. The SARRP is capable of delivering multiple arc small field irradiations of 220 keV X rays, and can produce radiation distributions comparable in size to a dose distribution produced by a brachytherapy source, but with a more uniform dose profile. Here the radiation doses were optimized to 2 Gy (5.6 Gy/min for 22 sec) and 4 Gy (5.5 Gy/min for 44 sec) to irradiate the cells, which were pretreated with Olaparib/NanoOlaparib for 24 hrs.

Nuclear localization and early DNA damage determination: To assess the early DNA Damage and PARP inhibition pathway damage, including PARP, PARylation, PARP cleavage and yH2AX in the cell lines to various treatment conditions, the prostate cancer cell lines were seeded at 100,000 cells, exposed to 20 μM Olaparib/NanoOlaparib, with and without radiation for both immunoflorescence (confocal) and western blotting assays. PARP-1 is a 116 kDa nuclear protein which is strongly activated by DNA strand breaks. During apoptosis, proteins such as caspase-3 and -7, cleave the PARP to yield an 85 kDa and a 25 kDa fragment. The nuclear localization and extent of apoptosis was determined using nuclear PARP cleavage assay and western blotting was used to determine the relative cellular concentrations of PARP, PAR, and yH2AX for various treatments on all the cell lines. Briefly, 105 cells/well were seeded in a 6 well plate on sterile coverslips for 24 hours before adding the drugs. The cells were incubated with the drugs for either 4 hr s after which they were irradiated. The cells thus treated were incubated at 37° C. for 1 hour before fixing them for further analysis.

Western blots for whole cell lysates: For western blotting, cell lysates were prepared with NP40 Buffer (Boston Bioproducts) supplemented with protease (Roche) and HALT phosphatase inhibitor cocktail (Thermo Scientific) and subsequently subjected to SDS-Gel separation (Invitrogen) and western blotting. The following antibodies were used for western blotting: anti-yH2AX (#9718, cell signalling), anti-PAR (Trevigen) anti-PARP (9542; Cell Signalling), and anti-6-Actin (AC-74; Sigma). The resulting western blots were quantified using Image J software. For image J analysis. The PAR concentration was first normalized to the loading actin control and then to the PARP-1 available in the treatment groups.

Nuclear PARP Cleavage assay using confocal microscopy: The cells were fixed with 1% formalin and kept at 37° C. for 15 min. The coverslips were given three PBS washings (3 min each) until the cells were free of fixing agent.

The cells were rehydrated using PBS with 0.5% tween 80 for 30 min, washed with buffer and incubated with Anti-PARP Cleavage Site (214/215) specific antibody, FITC Conjugate (Life technologies, NY, Cat #44-699) for 1 hour. This antibody specifically recognizes the 85 kDa fragment of cleaved PARP and can be used as a marker for detecting apoptotic cells. The coverslips were washed twice and were mounted onto the glass slide using and the edges were sealed using nail polish. The images were taken using an Olympus FV1000, multi-photon confocal microscope (Olympus America, Inc., Central Valley, Calif.). The excitation filters used for imaging cleaved PARP (FITC) and DAPI were Ex-488, 405 respectively. The emission filters were set at 530, 458 nm for FITC and DAPI respectively. All the images were captured with a 60× objective. Further analysis was performed in image J. A psuedo color was assigned to RGB format image where DAPI (green) and the cleaved PARP (red) and the merged images are reported in the following sections. Statistical significance was analyzed using two way ANOVA and Dunnet's multiple comparison tests in Graph Pad Prism.

Delayed viability assay after radiosensitization: Based on several studies, we modified the general clonogenic assay protocol to determine the long term effects of radio-sensitization with olaparib and NanoOlaparib (42, 43). The percent cell viability was determined using the modified clonogenic assay at 2 Gy and 4 Gy doses. Irradiation was carried out in prostate cancer cell lines, LNCaP PC3 and FKO1 as described above. Briefly, cells were seeded at 105 cells/well, incubated overnight and treated with Olaparib/NanoOlaparib equivalent to 20 uM Olaparib including all the relevant controls, irradiated after 4 hrs and left them in the incubator for 1 hour. The cells were then trypsinized and the cell suspensions of various treatments in duplicates were collected. The cell density was determined using automated cell counter and 10,000 and 20,000 cells from each treatment group was calculated and seeded in fresh 6 well plates. The cells were incubated for around 9 doubling cycles (specific) for each cell line and the colonies were fixed and stained using crystal violet stain. The excess stain was washed away using DI water and the images were taken using a digital camera. The stain was then dissolved in acetic acid to quantify the effect of Olaparib and NanoOlaparib treatments for all the cell lines.

Determination of Synergism using CalcuSyn: The fraction of cells affected (Fa) in response to Olaparib and Nanoolaparib treatment was determined as discussed in above sections. The fraction of cells affected by irradiation alone and the combination therapy was determined by the delayed cell viability assay and these values were utilized to perform synergyism analysis. A non-constant ratio combination design as formulated by CalcuSyn (Biosoft) based on the Chou-Talalay isobologram equation was used to calculate the Combination index (44). All the cells were exposed to 20 µM Olaparib or NanoOlaparib with increasing doses of Irradiation. The CI values were generated from isobolograms. All assays were performed in duplicates. Bars represent the Combination index (CI) of Olaparib and Nanoolaparib on LNCaP, PC3 and FKO1 in combinations with irradiation. The CI values generated for all the treatment groups are reported in the bar graphs are derived from duplicate experiments. The extent of synergism is postulated as indicated by the Chou-Talalay method. Combination index >1 represents increasingly additive and <1 represents increasingly synergistic, CI values between 0.1 to 0.3 or 0.3 to 0.7 indicate definite synergism but values ranging from 0.85 to 1.10 indicate slight synergism or additive effect.

Ptenpc−/−; Trp53pc−/−GEMM prostate cancer for in vivo characterization of NanoOlaparib: All the animals were maintained in the animal facilities of BIDMC/Harvard Medical School in accordance with institutional rules and ethical guidelines for experimental animal care. All animal experiments were approved by the BIDMC IACUC protocol 066-2011. The Ptenpc−/−; Trp53pc−/−GEMMs were developed as described previously (19, 45). Briefly, female PtenloxP/loxP; Trp53loxP/loxP mice were crossed with male PB-Cre4 transgenic mice for the prostate-specific deletion of Pten and Trp53. In the presence of Pb-Cre4, recombination of Pten and Trp53 was restricted to the three prostatic lobes, namely the anterior prostate, ventral prostate and dorsolateral prostate, with minor recombination occurring in seminal vesicles. It was observed that on combined inactivation of Pten and Trp53, HG-PIN was found in all three lobes from 100% of mice, and invasive prostate cancer in 50% of Ptenpc−/−; Trp53pc−/− mice by age 10 weeks (n=12). By 11 weeks, invasive adenocarcinoma was restricted to Ptenpc−/−; Trp53pc−/− mutants (19). For the preclinical assessment of the Olaparib vs. nanoOlaparib Ptenpc−/−; Trp53pc−/− mice were evaluated by MRI at 4 month of age for the presence of prostate tumours and subsequently enrolled. For in vivo therapeutic studies, Olaparib (LC Laboratories) in DMSO (50 mg/ml) was diluted in vehicle solution (10% 2-hydroxyl-propyl-βcyclodextrine (Sigma)/PBS) to a final injection volume of 10 µL/g body weight. Olaparib was administered daily by i.p. injection at a dose of 50 mg/kg. NanoOlaparib was injected i.p. directly from the stock (200 c.c) to achieve 50 mg/kg/administration.

Metabolomic Analysis: For LC/MS/MS of Olaparib pharmacokinetics metabolites were extracted from mouse tumor samples and analyzed as previously described (2, 46). Samples were measured using the Q1/Q3 transition of 435.2/281.3 for Olaparib. For the standard curve, Olaparib was prepared at 10-1 dilutions from 1 mM to 1 nM in 40% methanol. Concentration of Olaparib was normalized to weight of tumors.

MRI imaging and analysis: To monitor the tumor growth and therapeutic efficacy, mouse prostate images were acquired on an MRI scanner (Model M2 1T ASPECT Magnet Technologies Ltd., Netanya, Israel) and imaged as previously described (18). Tumour volume quantification was performed as previously described (47).

Histopathology: The mice were then sacrificed 2 weeks after the treatment, and the tumor, spleen, liver and kidney for Olaparib and NanoOlaparib groups were collected. Tissues were fixed in 4% paraformaldehyde and embedded in paraffin in accordance with standard procedures. 5-µm-thick tumor tissue sections were mounted onto a clean slide using microm HM 550 cryostat (Thermo Scientific, Pittsburgh, Pa.) and H&E staining was performed Embedding and H&E staining of sections was performed by the Histology Core at BIDMC.

Example 2: Formulation of Highly Condensed, Tumor pH Responsive NanoOlaparib

All the optimization steps were targeted towards formulating highly condensed pH responsive nanoformulation for Olaparib delivery, in order to obtain a ready-to-use injectable formulation, tailored for in vivo or in vitro studies at clinically relevant concentrations.

Figure 4A:
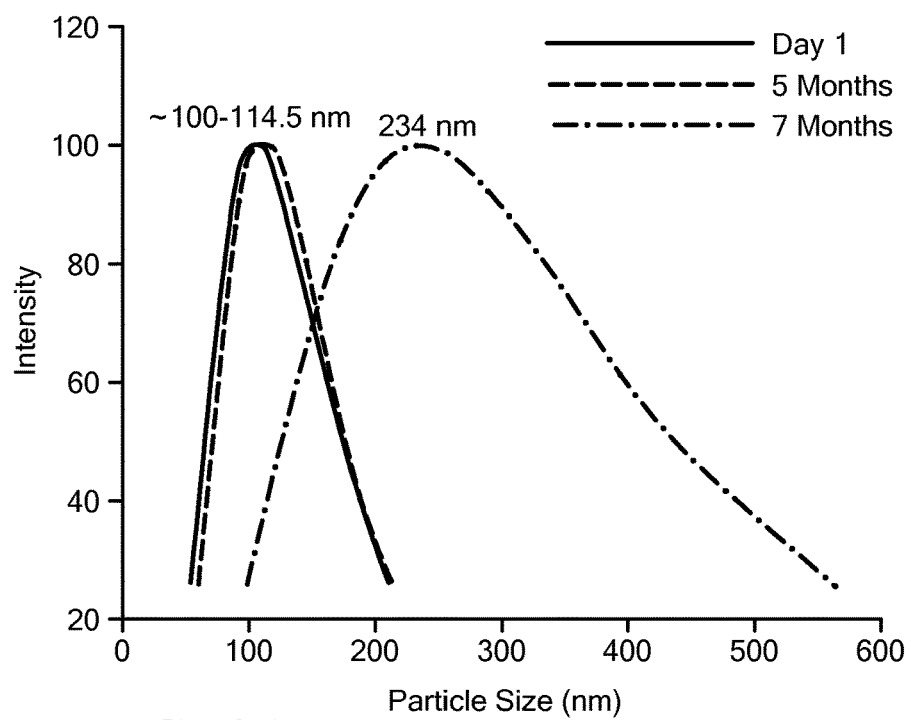
FIG. 4A is a graph showing the intensity-directed size distribution of a nanoparticulate formulation of olaparib after 24 hrs, 5 months, and 7 months of storage at 4° C.
Figure 4B:
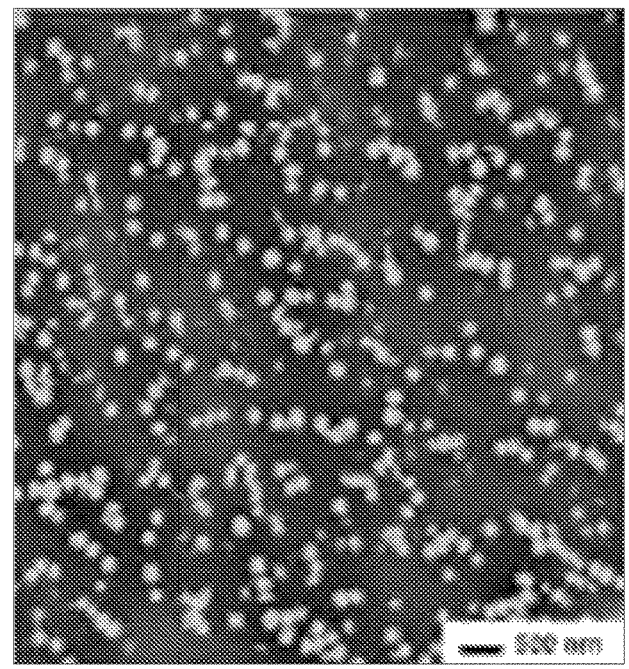
FIG. 4B is a transmission electron micrograph of nanoparticles containing olaparib stained with 1% uranyl acetate. Scale bar represents 500 nm.

The nanoparticle size distribution was analyzed with Transmission Electron Microscopy (TEM) (FIG. 4B) as seen across several batches was 100-120 nm and are in concert with the Dynamic Light Scattering (DLS) measurements (FIG. 4A). It is well known that the nanoparticles around this size range are most suitable for passive uptake of NanoOlaparib, specifically by leaky tumor vasculature (31, 32). The nanoparticle formulations are stable for at least 5 months, as confirmed by DLS measurement, but there was a significant increase in particle size after 7 months of storage at 4° C. (FIG. 4A).

Example 3: NanoOlaparib Shows Greater Drug Release at Tumor pH Compared to pH 7.4

Figure 4C:
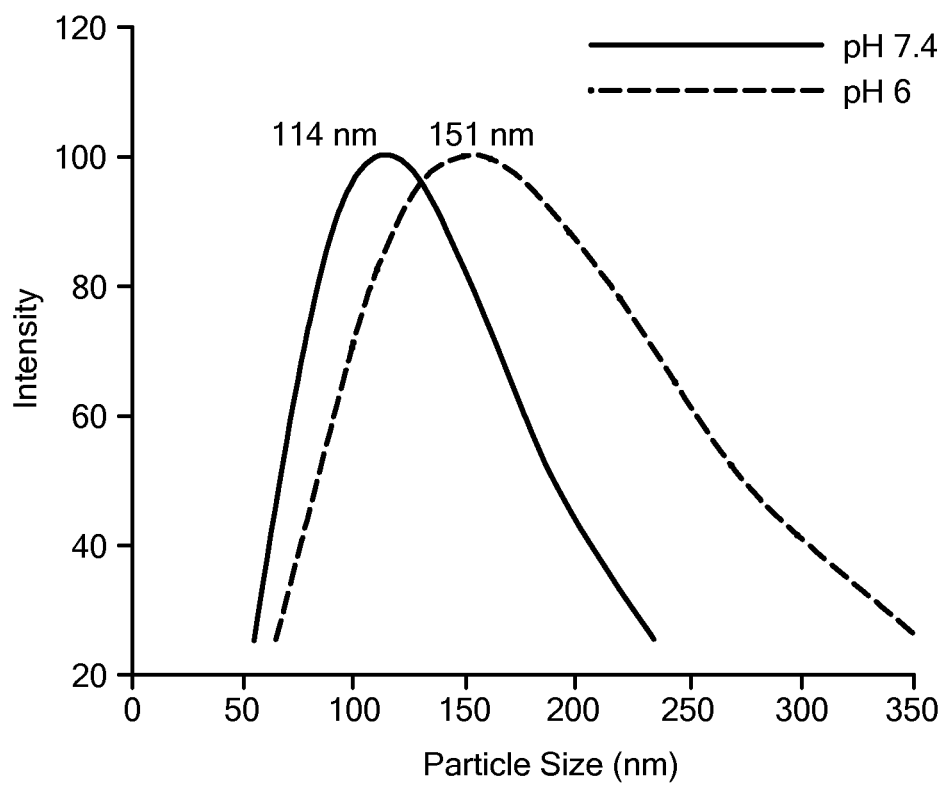
FIG. 4C is a graph showing the change in particle size distribution after incubation of nanoparticles containing olaparib in solvents with different pH.
Figure 4D:
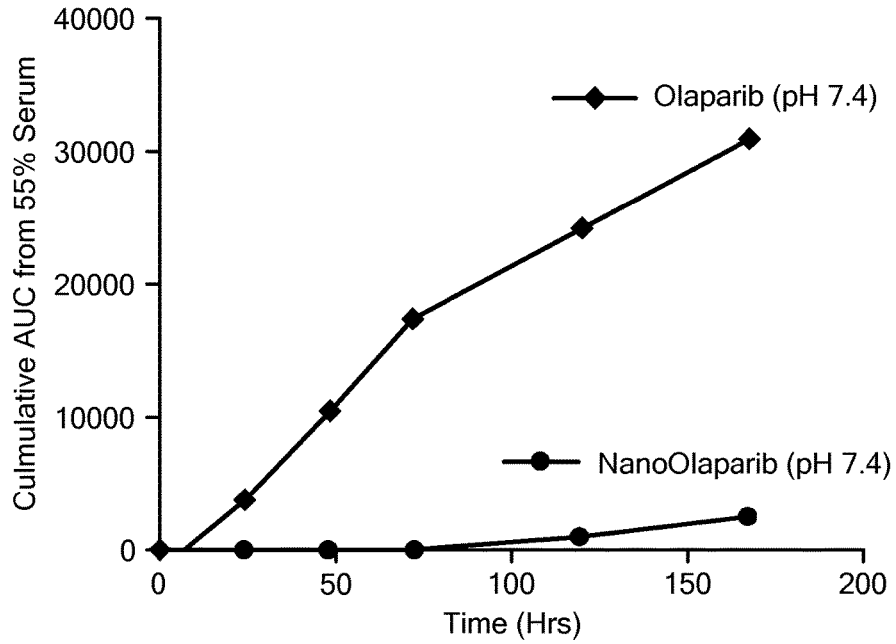
FIG. 4D is a graph showing the release profile of serum-associated nanoparticles containing olaparib with reference to olaparib in serum at pH 7.4 and 37° C. Values shown are the cumulative area under the curve (AUC) of the release buffer collected at the designated time points.
Figure 4E:
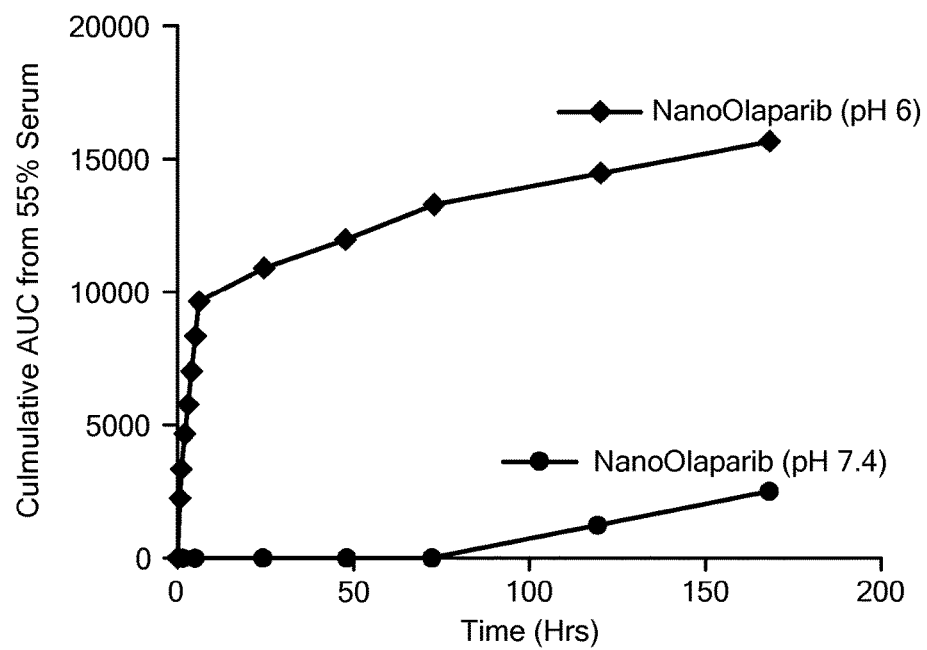
FIG. 4E is a graph showing the release profile of serum-associated nanoparticles containing olaparib at pH 6 and 37° C. with reference to olaparib in serum at pH 7.4. Values shown are the cumulative AUC of the release buffer collected at the designated time points.

The components of the nanoparticles were optimized such that the NanoOlaparib, in the presence of high serum media (simulating the blood concentration), would remain intact at pH 7.4 (blood), but show a burst release in response to acidic pH 6, which is prevalent in tumor microenvironment and endosomal organelles. Indeed NanoOlaparib demonstrated pH triggered release kinetics as seen in in vitro release studies of Olaparib and NanoOlaparib in serum at pH 7.4 and pH 6 (FIG. 4E). The release of Olaparib from the nanoparticle is 7.5 fold higher in tumor pH compared to the release of Olaparib at blood pH, in the presence of serum. The release profile of NanoOlaparib compared to the free Olaparib also implies a longer residence time in the blood for NanoOlaparib (FIG. 4D). The dynamics of elimination rate are not accounted for in these in vitro studies. It is believed that the abrupt increase in the size of NanoOlaparib at pH 6, allows for swelling of the outer layer of lipid nanoparticle, enabling the burst release at acidic pH trigger (FIG. 4C).

Example 4: Prostate Cancer Cell Lines for In Vitro Characterization of NanoOlaparib The efficacy of NanoOlaparib and Olaparib was analyzed in LNCaP, PC3 and FKO1 and simultaneously determined the differential levels of biomarkers of the PARP responses like PAR and yH2Ax. The results are discussed in Examples 5-6.

Example 5: NanoOlaparib Inhibits PARylation

Figure 5A:
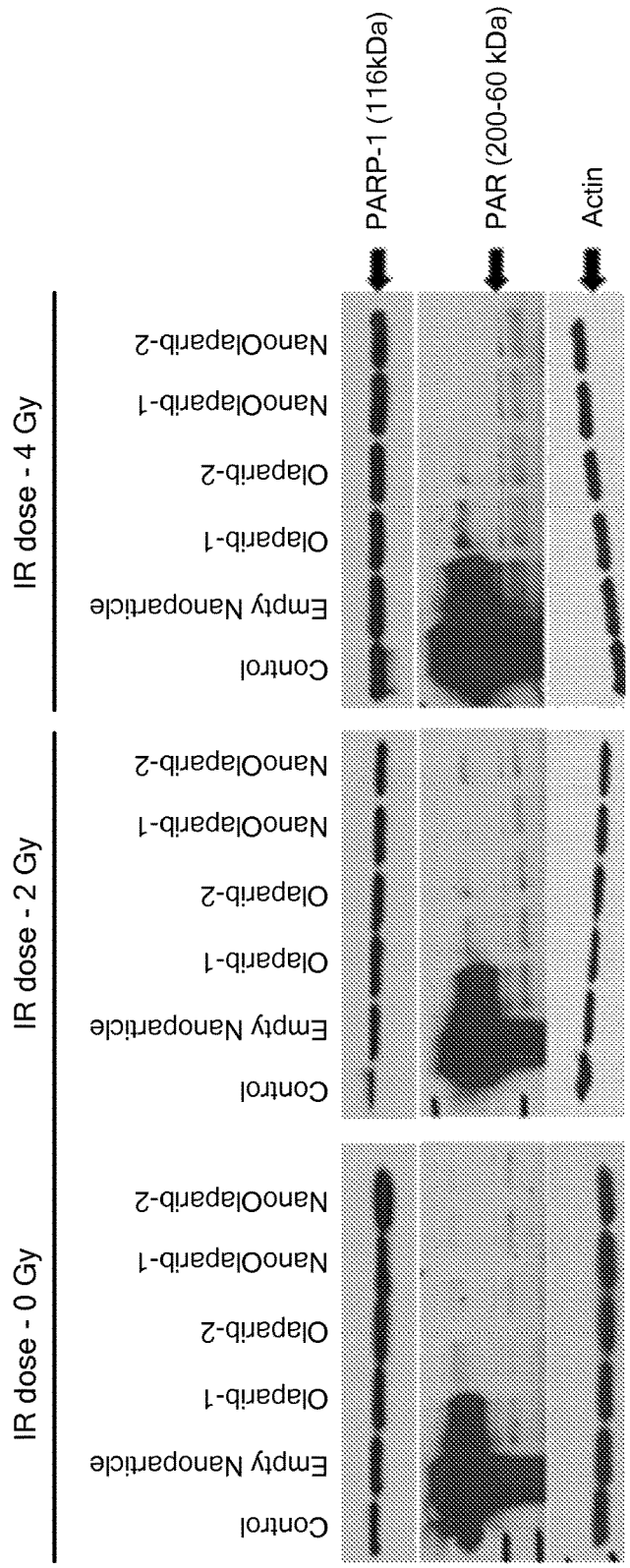
FIG. 5A shows western blots of PARP-1, PAR, and actin in extracts of PC3 cells. Cells were incubated with empty nanoparticles, olaparib (two samples), or NanoOlaparib (nanoparticles containing olaparib, two samples) for 4 hours, irradiated with 0, 2, or 4 Gy of ionizing X-rays, and incubated for 1 hour before extracts were prepared.
Figure 5B:
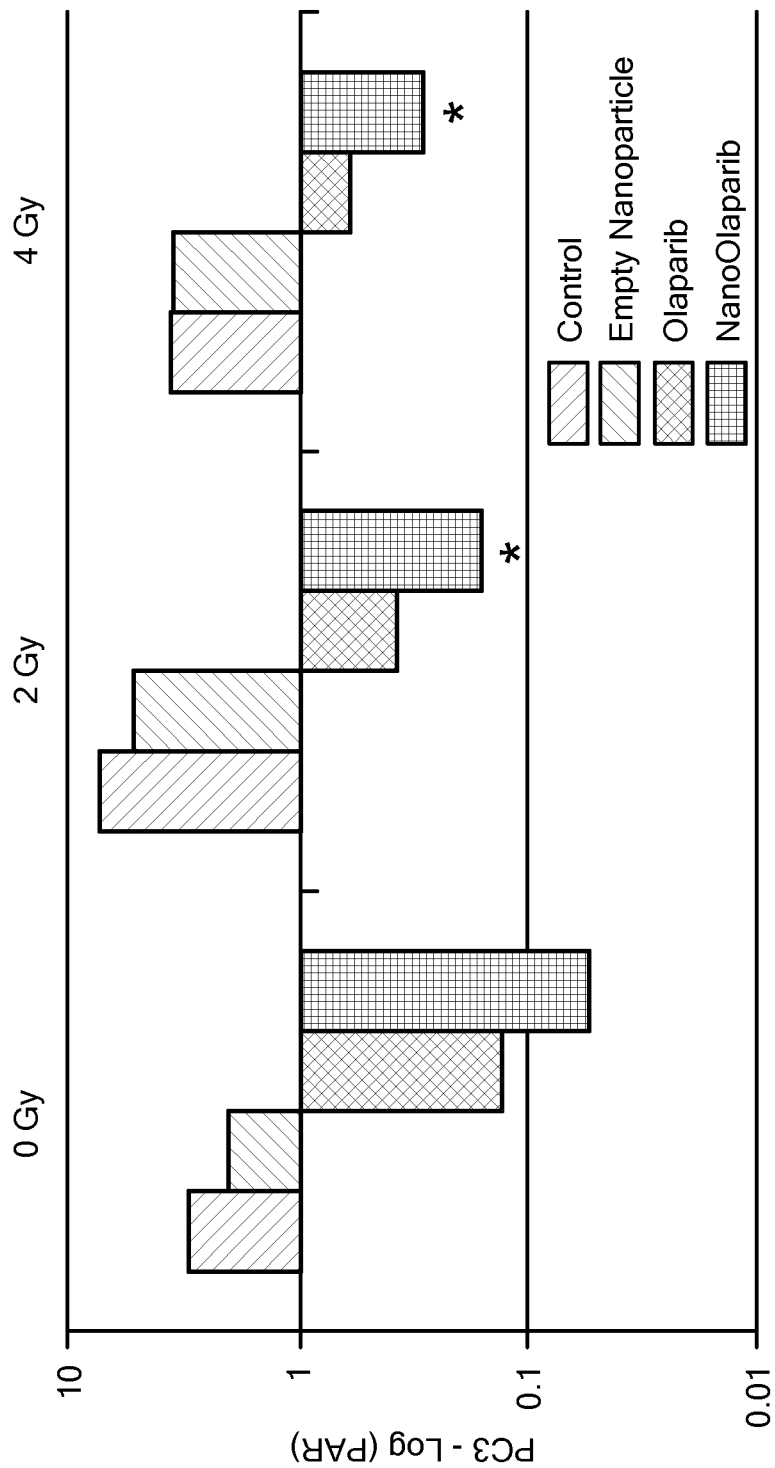
FIG. 5B is a graph of the quantified PAR signals from the western blots in FIG. 5A using the PARP-1 signal as a normalization standard. Star (*) indicates $p<0.05$ derived using unpaired 2 tailed t-test.

The PARP-1 cellular functions are enzymatically mediated by a negatively charged polymer, Poly ADP-Ribosyl (PAR) and can be used as the biomarker for evaluating the efficacy of PARP inhibition. In order to establish the functionality of the NanoOlaparib with or without concomitant irradiation, the whole cell lysates were analyzed to determine the PAR levels (PARylation) on the PC3 using western blot analysis. The PARylation blots of PC3 (FIG. 5A) show that, as early as 1 hour after the irradiation of the cells, pre-treated with NanoOlaparib, there was a greater abrogation of PARylation compared to Olaparib treated cells, potentially due to higher cellular uptake with NanoOlaparib. As expected, the increase in radiation dose from 0 Gy to 4 Gy also increased the PARylation, but the concentration of NanoOlaparib available for PARylation inhibition in the nucleus was greater than that of free Olaparib (FIG. 5B) in PC3.

Example 6: NanoOlaparib Increases Expression of yH2Ax

Figure 5C:
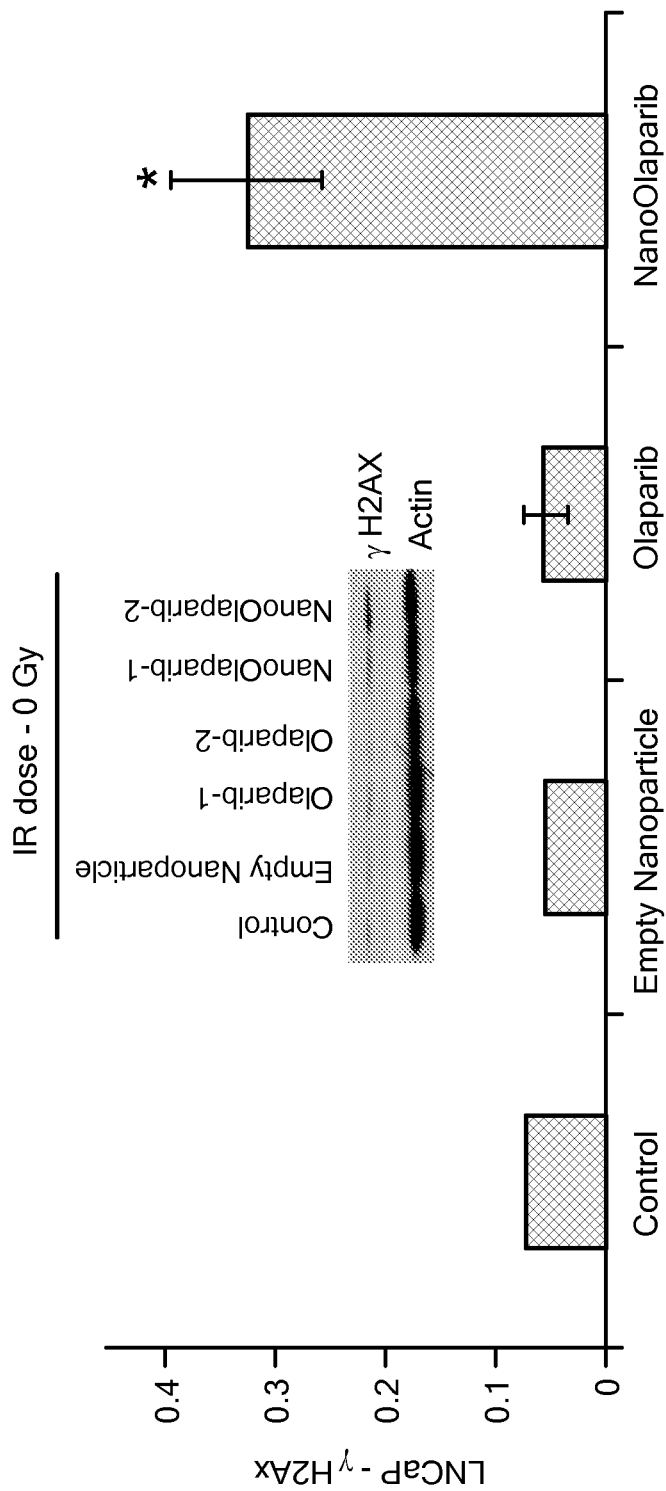
FIG. 5C shows western blots γH2AX and actin in extracts of PC3 cells and a graph of the quantified γH2AX signal using actin as a normalization standard. Cells were treated as in the non-irradiated samples in FIG. 5A. Star (*) indicates $p<0.05$ derived using an unpaired 2 tailed t-test.

The extensive cellular DNA repair machinery is regulated by recruitment of many cytosolic proteins including PARs and histones/histone variants (yH2Ax) (33). Here, the early expression of yH2Ax was studied in LNCaPs (FIG. 5C). yH2AX expression was the highest when LNCaPs were treated with NanoOlaparib, strengthening the hypothesis that, in vitro, NanoOlaparib has more favorable spatio-temporal availability compared to Olaparib so as to deter the repair processes (FIG. 3B).

Example 7: Nuclear Cleaved PARP Analysis Demonstrates Faster and Greater Nuclear Localization of NanoOlaparib PARP cleavage is considered to be one of the classical characteristics of apoptosis. The post irradiation apoptotic biomarkers like cleaved PARP are frequently dependent on fundamental events such as deterred DNA damage response, where PARP-1 plays a major role during the re-organization of chromatin in the nucleus (5). Hence the next step was to determine whether the NanoOlaparib is specifically delivering the drug to the nucleus and eliciting its inhibitory action on DNA damage repair pathway and/or apoptotic activity. The extent of cleaved PARP was determined 1 hr post irradiation using confocal analysis and studied the nuclear area and the expression of cleaved PARP in the Olaparib and NanoOlaparib treated cells with and without radiation. Maximum PARP cleavage was observed in cells treated with NanoOlaparib and irradiated at 2 Gy. In general, the extent of cleaved PARP followed a definite trend in all the cells lines tested, where irradiated cell <Olaparib treated cells +2 Gy cells treated with NanoOlaparib+2 Gy.

Figure 6A:
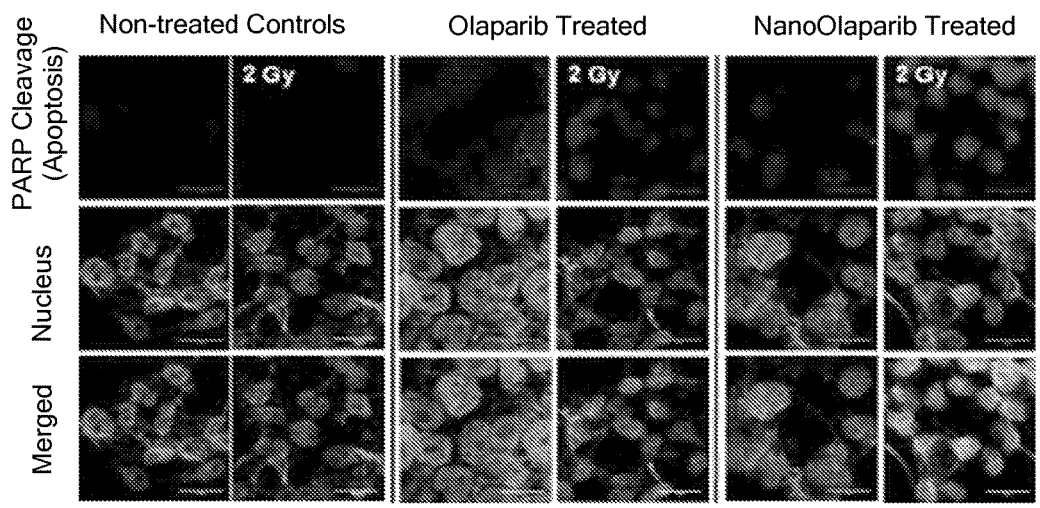
FIG. 6A shows fluorescence micrographs of LNCaP cells co-stained with DAPI and antibodies to cleaved PARP. DAPI staining of DNA is used to identify the nucleus. Cells were incubated with olaparib or NanoOlaparib for 4 hours, irradiated with 2 Gy of ionizing X-rays, and incubated for 1 hour before being process for microscopy. Bar represents 20 μm.
Figure 6B:
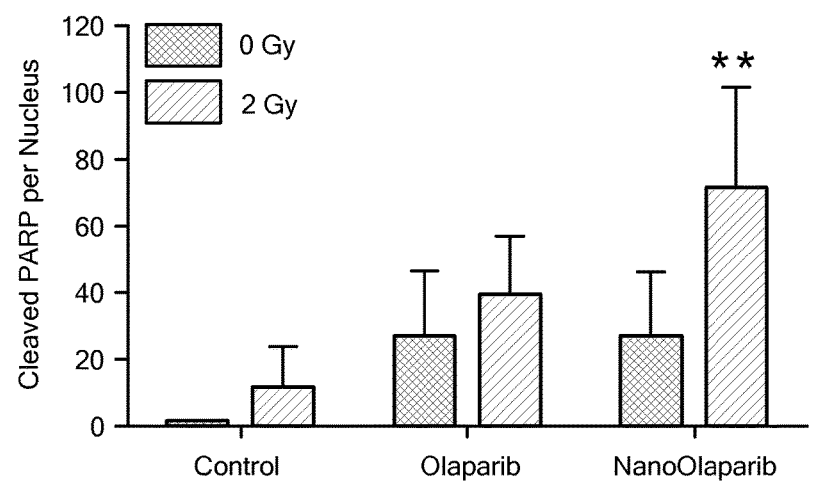
Figure 6C:
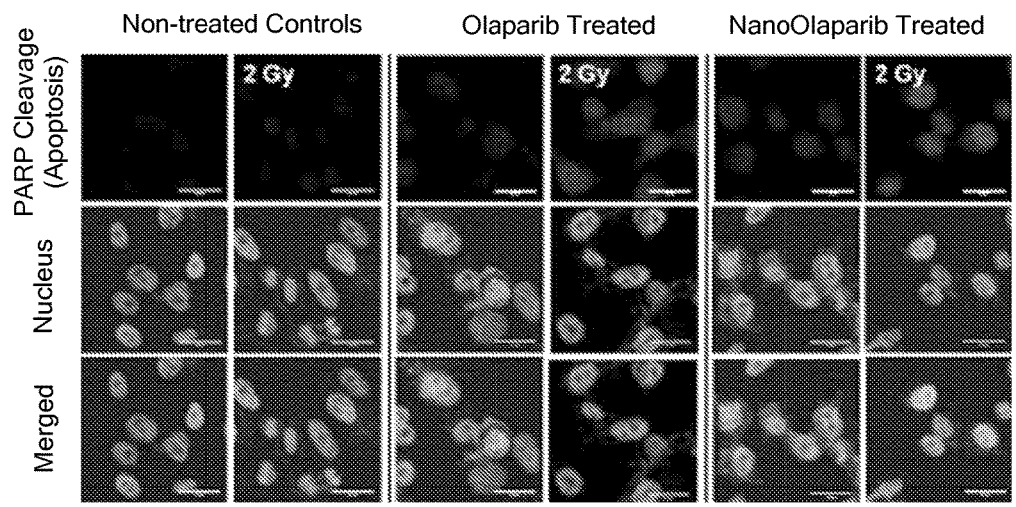
FIG. 6C shows fluorescence micrographs of PC3 cells co-stained with DAPI and antibodies to cleaved PARP. Cells were prepared as described for FIG. 6A. Bar represents 20 μm.
Figure 6D:
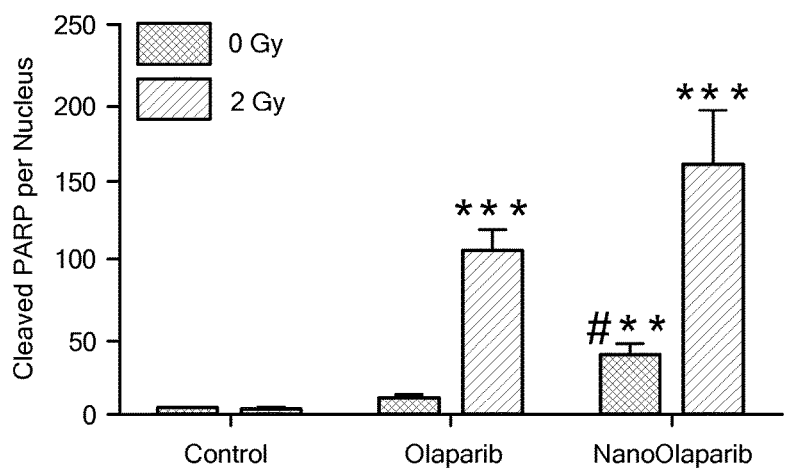
FIG. 6D is a graph showing quantification of cleaved PARP per nucleus. PC3 cells were treated as described for FIG. 6C except that a separate control sample was not irradiated. The symbol * indicates a statistically significant difference between the signals from both the olaparib 2Gy sample and the NanoOlaparib 2Gy sample, and the signal from the control 2Gy sample, with $P<0.001$. The symbol  indicates a statistically significant difference between the signal from the NanoOlaparib 0 Gy sample and the control 0 Gy sample. The symbol # indicates a statistically significant difference between the signal from the NanoOlaparib 0 Gy sample and the NanoOlaparib 2Gy sample.
Figure 6E:
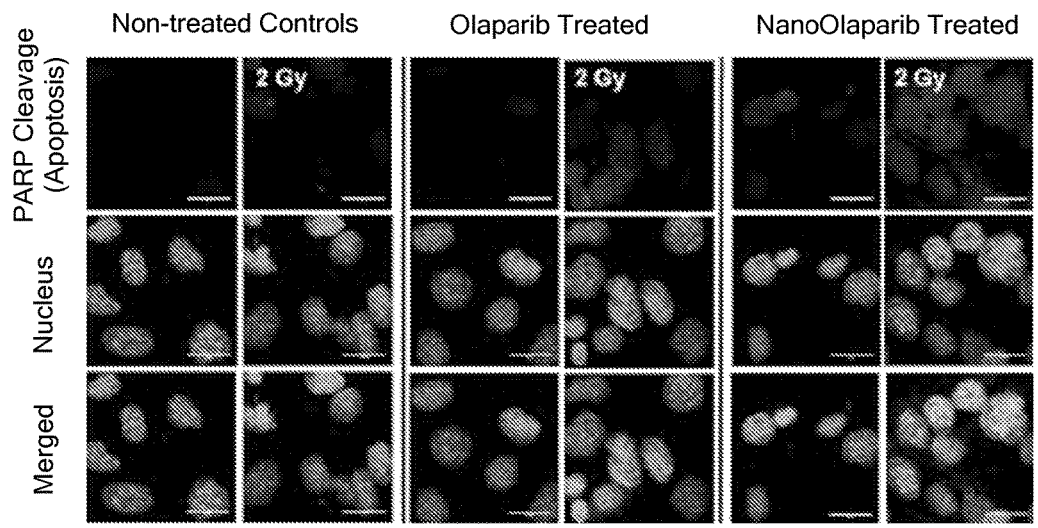
FIG. 6E shows fluorescence micrographs of FKO1 cells co-stained with DAPI and antibodies to cleaved PARP. Cells were prepared as described for FIG. 6A. Bar represents 20 μm.
Figure 6F:
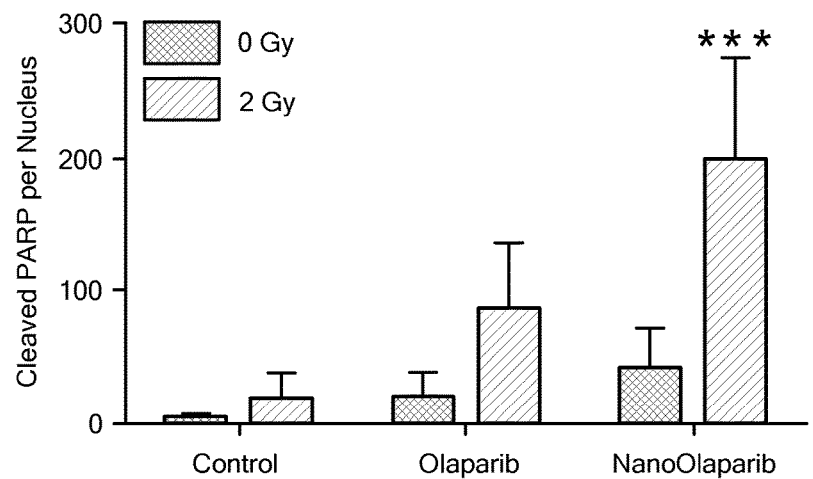
FIG. 6F is a graph showing quantification of cleaved PARP per nucleus. FKO1 cells were treated as described for FIG. 6E except that a separate control sample was not irradiated. The symbol *** indicates a statistically significant difference between the signal from the NanoOlaparib 2 Gy sample and the signal from the control 2 Gy sample, with $p<0.001$.
Figure 9A:
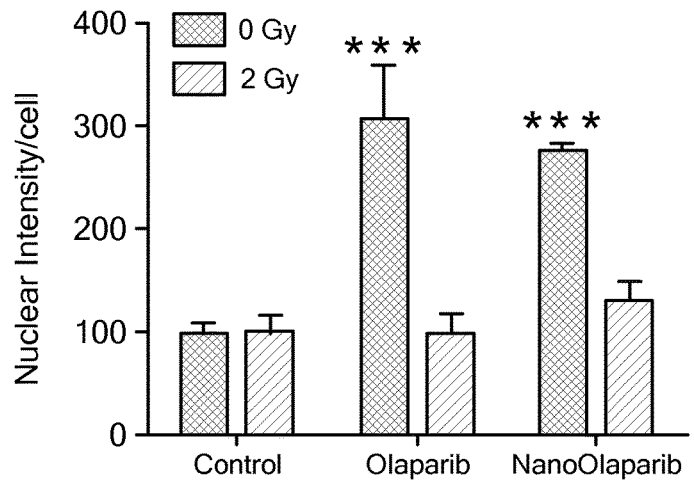
FIG. 9A is a graph showing nuclear size in LNCaP cells treated with olaparib or NanoOlaparib from the experiment described in FIG. 6A. Signals from DAPI staining of individual cells were quantified.
Figure 9B:
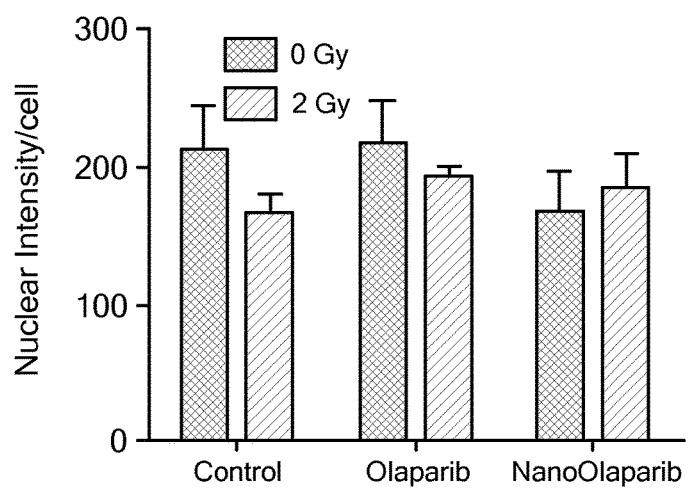
FIG. 9B is a graph showing nuclear size in PC3 cells treated with olaparib or NanoOlaparib from the experiment described in FIG. 6C.
Figure 9C:
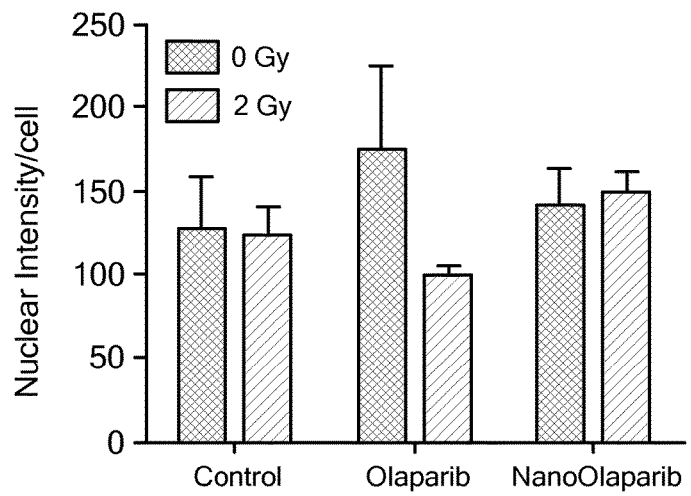
FIG. 9C is a graph showing nuclear size in FKO1 cells treated with olaparib or NanoOlaparib from the experiment described in FIG. 6E. Signals from DAPI staining of individual cells were quantified.

First, a 3-fold increase was observed in the nuclear area of LNCaP (green) after Olaparib/Nanoolaparib treatment (FIG. 9); in LNCaP cells, cleaved PARP (red) increased 20 fold upon monotherapy with both drugs, but in irradiated samples, a further 3 fold increase was seen only in NanoOlaparib treated cells (FIG. 6B). Also observed was that the cleaved PARP in the Olaparib treated LNCaPs was predominantly found in the perinuclear region, but in the same time frame, the NanoOlaparib treated cells clearly showed cleaved PARP activity inside the nucleus, stressing the importance of spacio-temporal delivery of Olaparib when used as a radiosensitizer. In PC3 cells, there was a ~10 fold increase in nuclear cleaved PARP in Nanoolaparib treated cells at 2 Gy and ~6 fold increase at 4 Gy compared to Olaparib treated counterparts (FIG. 6C, 6D). The irradiated FKO1 nuclei pre-treated with NanoOlaparib also showed a ~8 fold increase in nuclear cleaved PARP levels at 2 Gy and ~20 fold increase at 4 Gy compared to their respective Olaparib treated counterparts (FIG. 6E, 6F). No significant change in the nuclear size was seen in PC3 and FKO1 (FIG. 9). Empty nanoparticle controls induced very minimal cleaved PARP in the cell lines tested (not shown).

The early intervention of NanoOlaparib in the irradiation induced cell death pathways, is very evident from the above assay, which suggests that in all cell lines NanoOlaparib is a significantly better radiosensitizer compared to free Olaparib, which can be attributed to the greater and faster nuclear localization of Olaparib when delivered via nanoparticles (FIG. 3B).

Example 8: NanoOlaparib is a Better Radiosensitizer than Olaparib

Figure 7A:
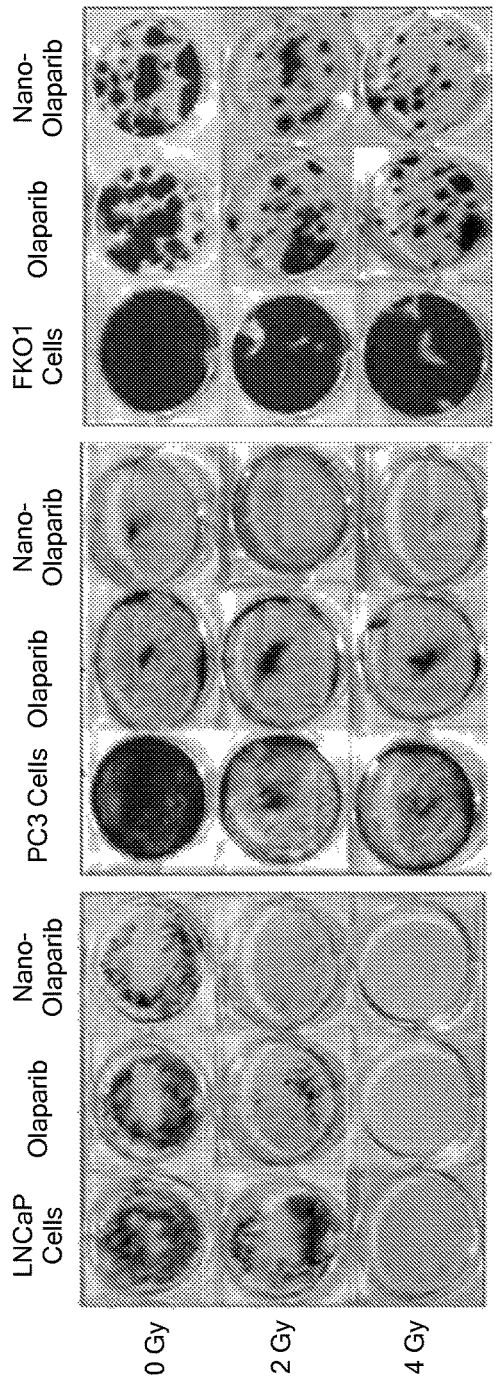
FIG. 7A shows photographs of culture dishes of cells treated with olaparib and NanoOlaparib prior to irradiation. LNCaP (left panel), PC3 (middle panel), and FKO1 (right panel) cells were incubated with olaparib or NanoOlaparib for four hours, irradiated with 0, 2 or 4 Gy of ionizing X-rays, cultured for 9 doubling cycles, and stained with crystal violet dye.
Figure 7B:
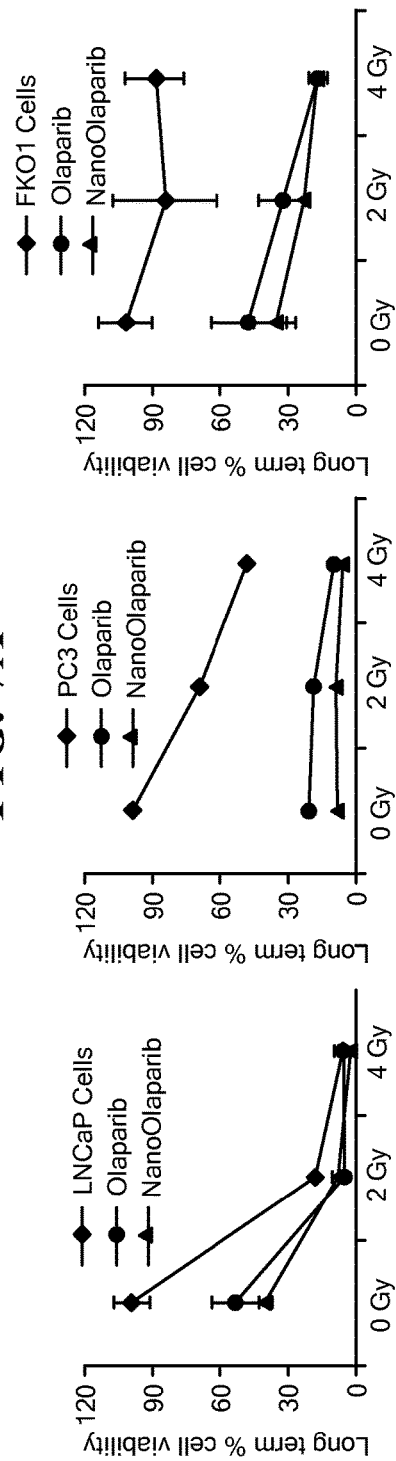
FIG. 7B shows graphs of cell viability from the experiment in FIG. 7A. Crystal violet dye was extracted from the samples and quantified by spectrometry at 590 nm.
Figure 7C:
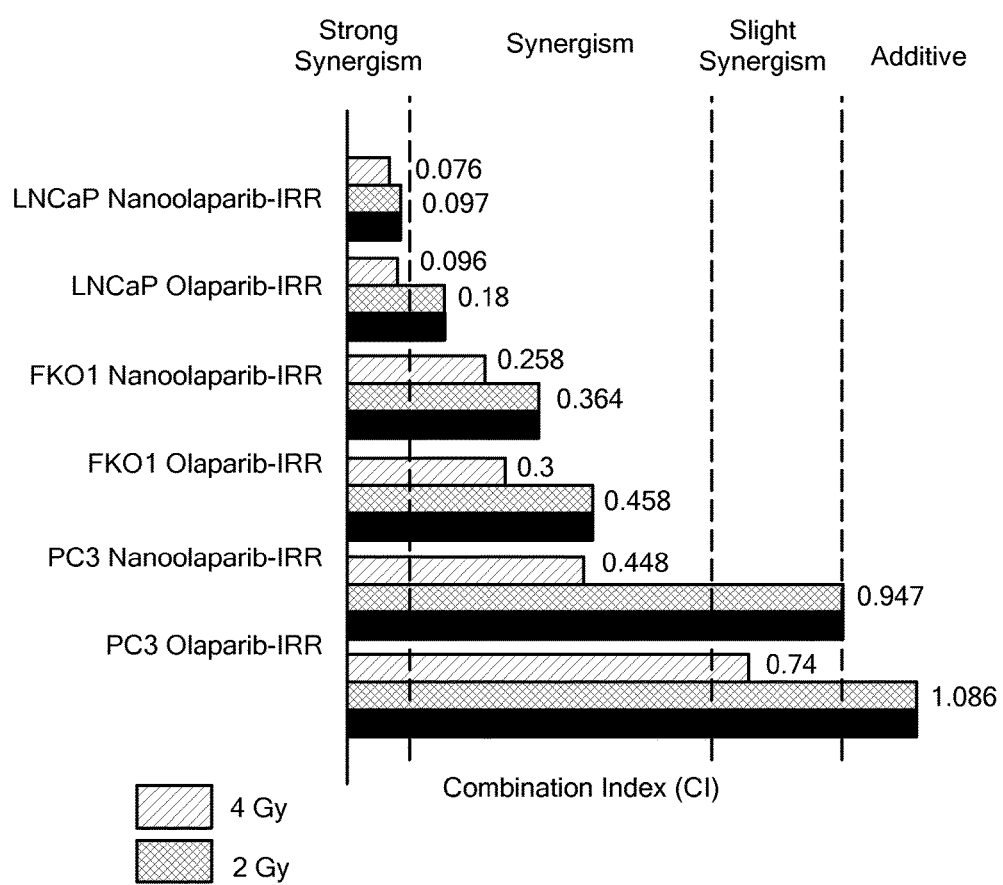
FIG. 7C is a bar graph showing the combinatorial effects of drug and irradiation treatment on LNCaP, PC3, and FKO1 cells. The combination index was determined using Calcusyn ver 2.0 based on the Chou-Talalay isobologram equation. Labels at the top of the graph indicate the level of synergy between drug and irradiation treatments.
Figure 7D:
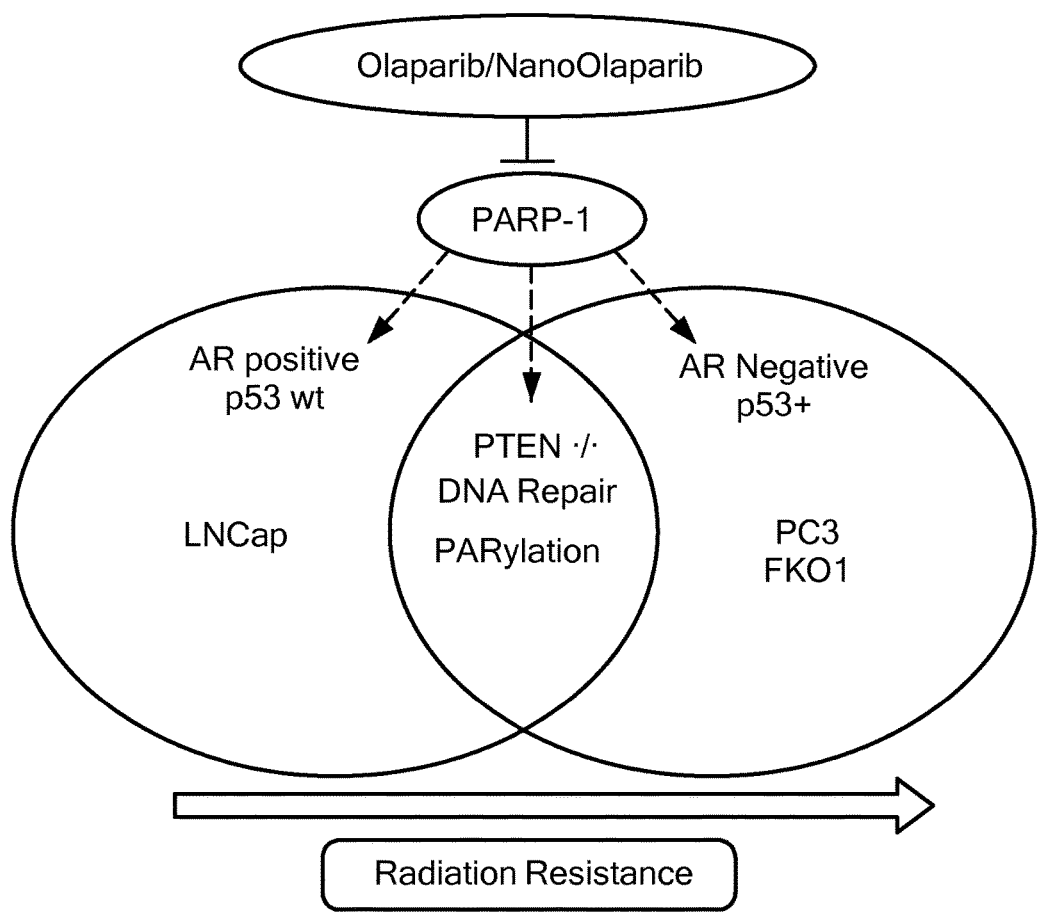
FIG. 7D is a schematic representation of the role of PARP in the in vitro prostate cancer models. p53 and PTEN genotypes and relative radiation resistance of LNCaP, PC3, and FKO1 cells are indicated.

To study the long term/delayed radiosensitizing efficacy of Olaparib and NanoOlaparib, the conventional clonogenic assay was modified to determine the long term percent cell viability of LNCaP, PC3 and FKO1 (FIG. 7A). In general, the radiosensitivity was observed to be highest for LNCaPs (80% cell death due to 2 Gy irradiation alone) followed by PC3 (30% cell death at 2 Gy) to FKO1s (17% cell death at 2 Gy), rendering FKO1 the most radioresistant of all the cell lines. The percent cell viability at 2 Gy show that the cells incubated with NanoOlaparib showed greater cell death (PC3s-90% and FKO1s-76%) compared to radiosensitization with Olaparib at the same dose (PC3s-80%, FKO1-68%). Similarly, the percent cell viability curves with NanoOlaparib treatments combined with 4 Gy radiation showed greater cell kill (LNCaPs-97%, PC3s-93% and FKO1s-83%) compared to radiosensitization with Olaparib at the same dose (LNCaPs-95%, PC3s-89%, FKO1-82%). The NanoOlaparib monotherapy also induced a significantly higher cell death (LNCaP-60%, PC3-91%, FKO1-64%) compared to treatment with Olaparib alone (LNCaP-46%, PC3-78%, FKO1-53%) (FIG. 7B). The key genetic traits and characteristics outline the rationale for our choice of prostate cancer cell lines, LNCAP, PC3 and FKO1 and the summary of the observations in this study (FIG. 7D).

Example 9: NanoOlaparib Shows Synergistic Activity with Radiation

The combination indices calculated using the CalcuSyn software (FIG. 7C), reveal that in all the cell lines and the treatments, Nanoolaparib has lower CI values (increasingly synergistic) compared to free Olaparib. The combination therapy appears to be highly synergistic in LNCaPs followed by FKO1's, while an additive effect is seen in PC3's when treated with Olaparib. FKO1 has the greatest benefit of NanoOlaparib treatment, considering its radioresistant nature and its synergism with the radiosensitization. In all the cell lines, an increase in synergism is observed at higher irradiation dose 4 Gy compared to 2 Gy, indicating that there is still room to increase the synergism in PC3 cells.

Example 10: NanoOlaparib(i.p.) Shows ~20 Times Higher Accumulation than Olaparib in Ptenpc−/−; Trp53pc−/− GEMMs of Prostate Cancer (Dorsal Prostate Lobes)

Figure 8A:
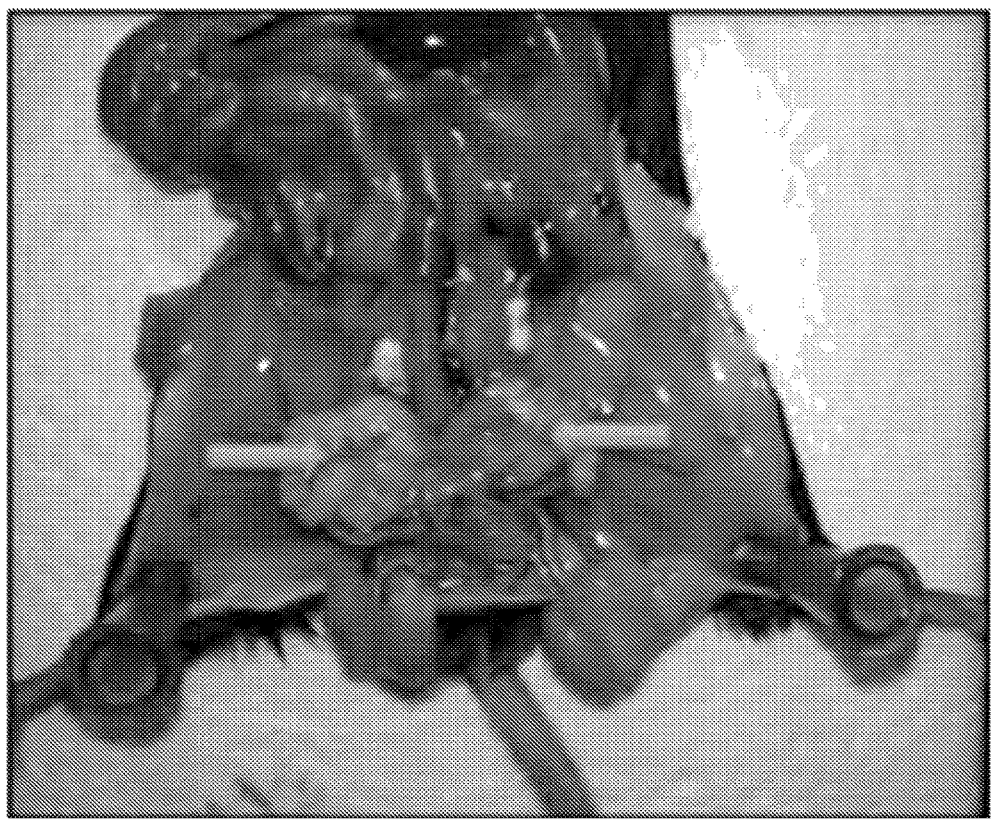
FIG. 8A shows a prostate tumor (arrows) in a Ptenpc−/− Trp53pc−/− mouse.
Figure 8B:
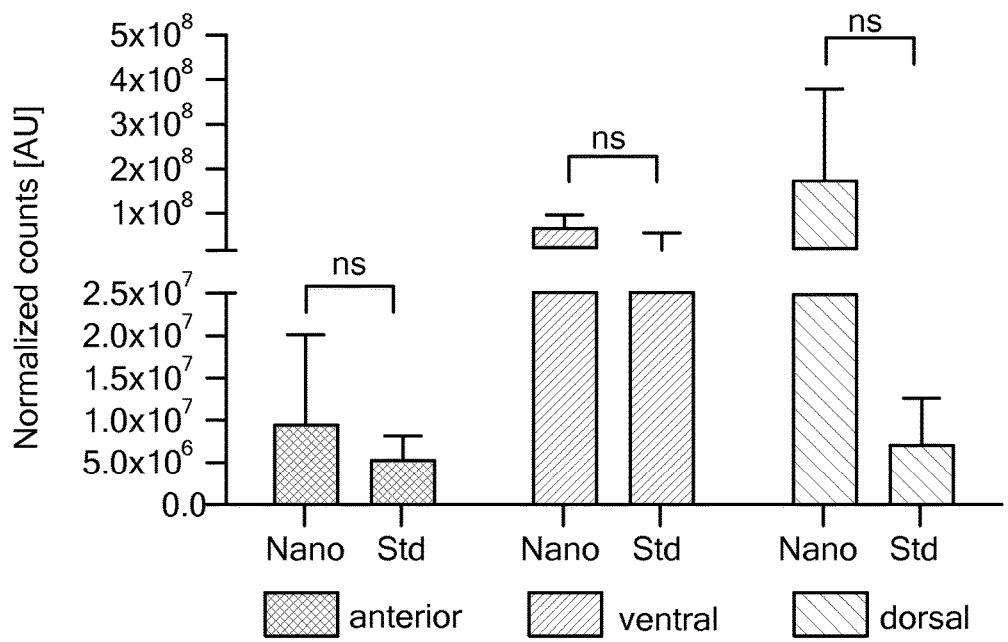
FIG. 8B is a graph showing olaparib metabolism in lobes of prostate tumors from mice treated with NanoOlaparib (Nano) or olaparib (Std). Metabolomic analysis of anterior, ventral, and dorsal lobes are shown in black, dark grey, and light grey, respectively. Counts were normalized to tumor weight.
Figure 8C:
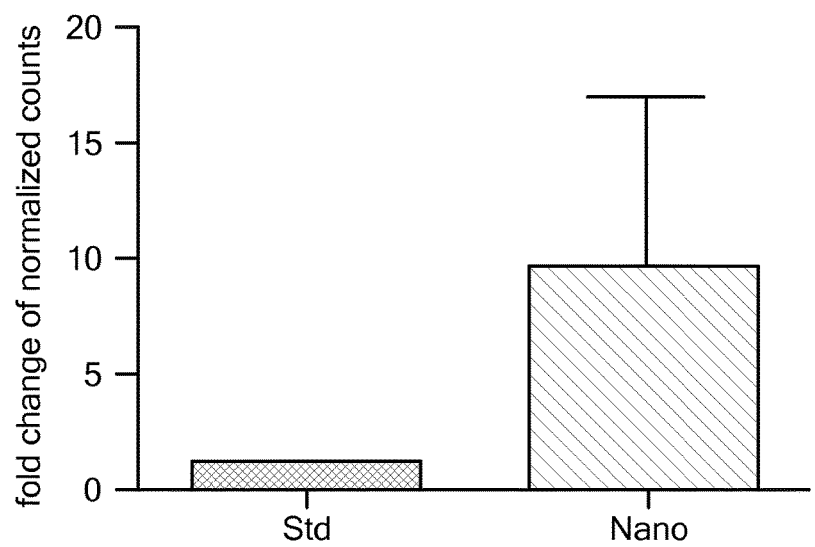
FIG. 8C is a graph of the increase in olaparib accumulation among the three lobes of the tumors analyzed in FIG. 8B.

The inventors reasoned that the GEMM mice with Ptenpc−/−; Trp53pc−/−, from which FKO1 cell line was derived would serve as an appropriate model of CRPC to investigate the tumor accumulation and therapeutic efficacy of NanoOlaparib (FIG. 8A). The prostate tumor accumulation of Olaparib and NanoOlaparib followed by 2 week treatment regimen was determined as mentioned in the methods section. The normalized Olaparib counts show greater Olaparib accumulation, via nano delivery compared to the free drug administration in all the prostate lobes (FIG. 8B). The fold increase in accumulation of NanoOlaparib is determined to be ~20 fold in dorsal prostate lobes and the average accumulation in all lobes is ~10 times higher than that of free Olaparib when administered i.p. (FIG. 8C).

Figure 8D:
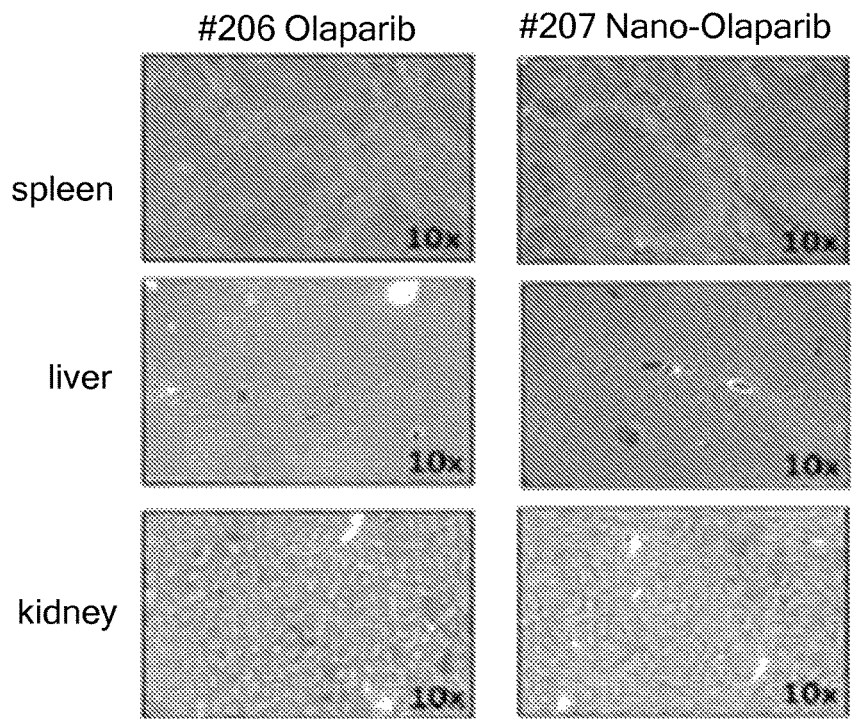
FIG. 8D shows histopathological images of spleen, liver, and kidney tissues from mice treated for two weeks with either olaparib or NanoOlaparib.
Figure 8E:
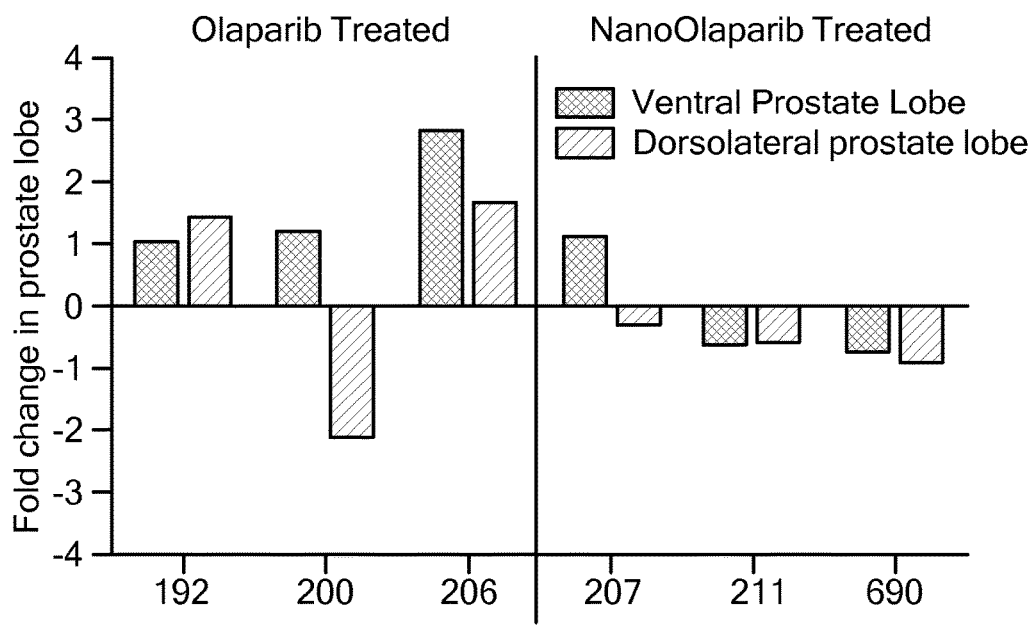
FIG. 8E is a graph showing the change in volume of lobes of tumors in mice treated with olaparib or NanoOlaparib. Volumes of ventral and dorsolateral lobes are shown in black and grey, respectively. Changes in volume are shown in units of $\log_2$ of the change in volume.

Example 11: NanoOlaparib Decreases the Tumor Volume in Ptenpc−/−; Trp53pc−/−GEMMs of Prostate Cancer As discussed in the earlier sections, gene ablations of both tumor suppressors PTEN and p53, are correlated with cancers progressing to castration resistant prostate cancers (CRPC) (27-29). The therapeutic response of olaparib and NanoOlaparib treatments are reported here in terms of fold change in the volumes of dorsolateral and ventral prostate lobes (FIG. 8D) in the in vivo GEMMs, employing MRI analysis as mentioned in the above sections. In general, the solid tumor is the most aggressive subpopulation of the tumor, thus the fold change in solid tumor volumes is reported here. The fold change in the ventral and dorsolateral prostate lobe volumes was analyzed 14 days after treatments, compared to the nontreated tumors on day 1. While free Olaparib shows a ~1.5 to 2.5 fold increase in the tumor bearing lobes, NanoOlaparib treatment not only stabilized the tumors, but also decreased the tumor volumes ~1.5 fold in the dorsolateral lobes, where there was highest accumulation (~20 fold higher than free Olaparib) of NanoOlaparib (FIG. 8B).

Example 12: NanoOlaparib Shows Minimal Toxicity in Primary RES Organs

The toxicity profile of the NanoOlaparib in the RES organs (FIG. 8C) was investigated. The H&E staining of liver, kidney and spleen doesn't show any significant differences between the Olaparib treated mice (mouse ID 206) and NanoOlaparib treated mice (mouse ID 207), rendering NanoOlaparib a safe vehicle for i.p. administration. A preliminary study investigating the toxicity of empty nanoparticles (vehicle) was carried out in 3 mice. No body weight loss or morphological changes were seen (data not reported) in those studies.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

1. Audeh M W, Carmichael J, Penson R T, Friedlander M, Powell B, Bell-McGuinn K M, et al. Oral poly(ADP-ribose) polymerase inhibitor olaparib in patients with BRCA1 or BRCA2 mutations and recurrent ovarian cancer: a proof-of-concept trial. Lancet. 2010; 376:245-51.
2. Juvekar A, Burga L N, Hu H, Lunsford E P, Ibrahim Y H, Balmana J, et al. Combining a PI3K inhibitor with a PARP inhibitor provides an effective therapy for BRCA1-related breast cancer. Cancer discovery. 2012; 2:1048-63.
3. Tutt A, Robson M, Garber J E, Domchek S M, Audeh M W, Weitzel J N, et al. Oral poly(ADP-ribose) polymerase inhibitor olaparib in patients with BRCA1 or BRCA2 mutations and advanced breast cancer: a proof-of-concept trial. Lancet. 2010; 376:235-44.
4. Gelmon K A, Tischkowitz M, Mackay H, Swenerton K, Robidoux A, Tonkin K, et al. Olaparib in patients with recurrent high-grade serous or poorly differentiated ovarian carcinoma or triple-negative breast cancer: a phase 2, multicentre, open-label, non-randomised study. The lancet oncology. 2011; 12:852-61.
5. Kim M Y, Zhang T, Kraus W L. Poly(ADP-ribosyl)ation by PARP-1: 'PAR-laying' NAD+ into a nuclear signal. Genes & development. 2005; 19:1951-67.
6. Luo X, Kraus W L. On PAR with PARP: cellular stress signaling through poly(ADP-ribose) and PARP-1. Genes & development. 2012; 26:417-32.

7. Ashworth A. A synthetic lethal therapeutic approach: poly(ADP) ribose polymerase inhibitors for the treatment of cancers deficient in DNA double-strand break repair. Journal of clinical oncology:official journal of the American Society of Clinical Oncology. 2008; 26:3785-90.
8. Hirai T, Shirai H, Fujimori H, Okayasu R, Sasai K, Masutani M. Radiosensitization effect of poly(ADP-ribose) polymerase inhibition in cells exposed to low and high liner energy transfer radiation. Cancer science. 2012; 103:1045-50.
9. Senra J M, Telfer B A, Cherry K E, McCrudden C M, Hirst D G, O'Connor M J, et al. Inhibition of PARP-1 by olaparib (AZD2281) increases the radiosensitivity of a lung tumor xenograft. Molecular cancer therapeutics. 2011; 10:1949-58.
10. Miura K, Sakata K-i, Someya M, Matsumoto Y, Matsumoto H, Takahashi A, et al. The combination of olaparib and camptothecin for effective radiosensitization. Radiation Oncology. 2012; 7:62.
11. Han S, Brenner J C, Sabolch A, Jackson W, Speers C, Wilder-Romans K, et al. Targeted radiosensitization of ETS fusion-positive prostate cancer through PARP1 inhibition. Neoplasia (New York, N.Y.). 2013; 15:1207-17.
12. Barreto-Andrade J C, Efimova E V, Mauceri H J, Beckett M A, Sutton H G, Darga T E, et al. Response of Human Prostate Cancer Cells and Tumors to Combining PARP Inhibition with Ionizing Radiation. Molecular cancer therapeutics. 2011; 10:1185-93.
13. Dong Y, Bey E A, Li L S, Kabbani W, Yan J, Xie X J, et al. Prostate cancer radiosensitization through poly (ADP-Ribose) polymerase-1 hyperactivation. Cancer research. 2010; 70:8088-96.
14. Olaparib shows promise in multiple tumor types. Cancer discovery. 2013; 3:OF5.
15. Bundred N, Gardovskis J, Jaskiewicz J, Eglitis J, Paramonov V, McCormack P, et al. Evaluation of the pharmacodynamics and pharmacokinetics of the PARP inhibitor olaparib: a phase I multicentre trial in patients scheduled for elective breast cancer surgery. Investigational new drugs. 2013; 31:949-58.
16. Garcia K P, Zarschler K, Barbaro L, Barreto J A, O'Malley W, Spiccia L, et al. Zwitterionic-Coated "Stealth" Nanoparticles for Biomedical Applications: Recent Advances in Countering Biomolecular Corona Formation and Uptake by the Mononuclear Phagocyte System. Small (Weinheim an der Bergstrasse, Germany). 2014.
17. Staropoli N, Ciliberto D, Botta C, Fiorillo L, Grimaldi A, Lama S, et al. Pegylated liposomal doxorubicin in the manaGEMMent of ovarian cancer: A systematic review and metaanalysis of randomized trials. Cancer biology & therapy. 2014; 15.
18. Lunardi A, Ala U, Epping M T, Salmena L, Clohessy J G, Webster K A, et al. A co-clinical approach identifies mechanisms and potential therapies for androgen deprivation resistance in prostate cancer. Nature genetics. 2013; 45:747-55.
19. Chen Z, Trotman L C, Shaffer D, Lin H K, Dotan Z A, Niki M, et al. Crucial role of p53-dependent cellular senescence in suppression of Pten-deficient tumorigenesis. Nature. 2005; 436:725-30.
20. Kirby M, Hirst C, Crawford E D. Characterising the castration-resistant prostate cancer population: a systematic review. International journal of clinical practice. 2011; 65:1180-92.
21. Mazzucchelli R, Scarpelli M, Lopez-Beltran A, Cheng L, Di Primio R, Montironi R. Treatment effects in prostate cancer following traditional and emerging therapies. International journal of immunopathology and pharmacology. 2013; 26:291-8.
22. Won A C, Gurney H, Marx G, De Souza P, Patel M I. Primary treatment of the prostate improves local palliation in men who ultimately develop castrate-resistant prostate cancer. BJU international. 2013; 112:E250-5.
23. Oplustilova L, Wolanin K, Mistrik M, Korinkova G, Simkova D, Bouchal J, et al. Evaluation of candidate biomarkers to predict cancer cell sensitivity or resistance to PARP-1 inhibitor treatment. Cell cycle (Georgetown, Tex.). 2012; 11:3837-50.
24. Fraser M, Zhao H, Luoto K R, Lundin C, Coackley C, Chan N, et al. PTEN deletion in prostate cancer cells does not associate with loss of RAD51 function: implications for radiotherapy and chemotherapy. Clinical cancer research: an official journal of the American Association for Cancer Research. 2012; 18:1015-27.
25. Schiewer M J, Goodwin J F, Han S, Brenner J C, Augello M A, Dean J L, et al. Dual roles of PARP-1 promote cancer growth and progression. Cancer discovery. 2012; 2:1134-49.
26. Chatterjee P, Choudhary G S, Sharma A, Singh K, Heston W D, Ciezki J, et al. PARP inhibition sensitizes to low dose-rate radiation TMPRSS2-ERG fusion gene-expressing and PTEN-deficient prostate cancer cells. PloS one. 2013; 8:e60408.
27. Martin T J, Peer C J, Figg W D. Uncovering the genetic landscape driving castration-resistant prostate cancer. Cancer biology & therapy. 2013; 14:399-400.
28. Phin S, Moore M W, Cotter P D. Genomic RearranGEMMents of in Prostate Cancer. Frontiers in oncology. 2013; 3:240.
29. Grasso C S, Wu Y M, Robinson D R, Cao X, Dhanasekaran S M, Khan A P, et al. The mutational landscape of lethal castration-resistant prostate cancer. Nature. 2012; 487:239-43.
30. Ittmann M, Huang J, Radaelli E, Martin P, Signoretti S, Sullivan R, et al. Animal models of human prostate cancer: the consensus report of the New York meeting of the Mouse Models of Human Cancers Consortium Prostate Pathology Committee. Cancer research. 2013; 73:2718-36.
31. Jain R K. Delivery of molecular and cellular medicine to solid tumors. Advanced Drug Delivery Reviews. 2001; 46:149-68.
32. Campbell R B, Fukumura D, Brown E B, Mazzola L M, Izumi Y, Jain R K, et al. Cationic charge determines the distribution of liposomes between the vascular and extravascular compartments of tumors. Cancer research. 2002; 62:6831-6.
33. Rogakou E, Nieves-Neira W, Boon C, Pommier Y, Bonner W. Initiation of DNA fragmentation during apoptosis induces phosphorylation of H2AX histone at serine 139. J Biol Chem. 2000; 275:9390-5.
34. Polkinghorn W R, Parker J S, Lee M X, Kass E M, Spratt D E, Iaquinta P J, et al. Androgen receptor signaling regulates DNA repair in prostate cancers. Cancer discovery. 2013; 3:1245-53.
35. Vitale I, Galluzzi L, Castedo M, Kroemer G. Mitotic catastrophe: a mechanism for avoiding genomic instability. Nature reviews Molecular cell biology. 2011; 12:385-92.
36. Riganti C, Voena C, Kopecka J, Corsetto P A, Montorfano G, Enrico E, et al. Liposome-encapsulated doxorubicin reverses drug resistance by inhibiting P-glycoprotein in human cancer cells. Molecular pharmaceutics. 2011; 8:683-700.
37. Fedoruk M N, Giménez-Bonafé P, Guns E S, Mayer L D, Nelson C C. P-glycoprotein increases the efflux of the androgen dihydrotestosterone and reduces androgen responsive gene activity in prostate tumor cells. The Prostate. 2004; 59:77-90.
38. Zietman A L, Bae K, Slater J D, Shipley W U, Efstathiou J A, Coen J J, et al. Randomized trial comparing conventional-dose with high-dose conformal radiation therapy in early-stage adenocarcinoma of the prostate: long-term results from proton radiation oncology group/american college of radiology 95-09. Journal of clinical oncology: official journal of the American Society of Clinical Oncology. 2010; 28:1106-11.
39. Kuban D A, Tucker S L, Dong L, Starkschall G, Huang E H, Cheung M R, et al. Long-term results of the M. D. Anderson randomized dose-escalation trial for prostate cancer. International journal of radiation oncology, biology, physics. 2008; 70:67-74.
40. Shappell S B, Thomas G V, Roberts R L, Herbert R, Ittmann M M, Rubin M A, et al. Prostate Pathology of Genetically Engineered Mice: Definitions and Classification. The Consensus Report from the Bar Harbor Meeting of the Mouse Models of Human Cancer Consortium Prostate Pathology Committee. Cancer research. 2004; 64:2270-305.
41. Lee H J, Yoon C, Schmidt B, Park do J, Zhang A Y, Erkizan H V, et al. Combining PARP-1 inhibition and radiation in ewing sarcoma results in lethal DNA damage. Molecular cancer therapeutics. 2013; 12:2591-600.
42. Abazeed M E, Adams D J, Hurov K E, Tamayo P, Creighton C J, Sonkin D, et al. Integrative Radiogenomic Profiling of Squamous Cell Lung Cancer. Cancer research. 2013; 73:6289-98.
43. Buch K, Peters T, Nawroth T, Sanger M, Schmidberger H, Langguth P. Determination of cell survival after irradiation via clonogenic assay versus multiple MTT Assay—A comparative study. Radiation Oncology. 2012; 7:1.
44. Chou T-C. Drug Combination Studies and Their Synergy Quantification Using the Chou-Talalay Method. Cancer research. 2010; 70:440-6.
45. Trotman L C, Niki M, Dotan Z A, Koutcher J A, Di Cristofano A, Xiao A, et al. Pten Dose Dictates Cancer Progression in the Prostate. PLoS Biol. 2003; 1:e59.
46. Yuan M, Breitkopf S B, Yang X, Asara J M. A positive/negative ion-switching, targeted mass spectrometry-based metabolomics platform for bodily fluids, cells, and fresh and fixed tissue. Nature protocols. 2012; 7:872-81.
47. Nastiuk K L, Liu H, Hamamura M, Muftuler L T, Nalcioglu O, Krolewski J J. In vivo MRI volumetric measurement of prostate regression and growth in mice. BMC urology. 2007; 7:12.

What is claimed is:

1. A nanoparticulate formulation of an inhibitor of a poly (ADP-ribose) polymerase (PARP) enzyme, the formulation comprising a suspension of lipid vesicles in an aqueous medium, wherein the lipid vesicles have a positive surface charge, have an average diameter in the range from about 50 nm to about 200 nm, comprise a PARP inhibitor selected from olaparib and BMN-673, and comprise a PEGylated lipid moiety, wherein the effective concentration of the PARP inhibitor within the lipid vesicles is in the range from about 400 µM to about 20 mM for olaparib or in the range from about 50 nM to about 1 µM for BMN-673.

2. The nanoparticulate formulation of claim 1 further comprising an additional pharmaceutical agent within the lipid vesicles.

3. The nanoparticulate formulation of claim 2, wherein the additional pharmaceutical agent is cisplatin, temozolomide, gemcitabine, doxorubicin, a PI3K inhibitor, a MEK inhibitor, an ATM inhibitor, or another anti-cancer agent.

4. The nanoparticulate formulation of claim 1, wherein the lipid vesicles comprise a lipid that is positively charged at pH 7.4.

5. The nanoparticulate formulation of claim 4, wherein the positively charged lipid is N-[1-(2,3-dioleoyloxy)propyl]-N,N,N-trimethylammonium methyl sulfate (DOTAP).

6. The nanoparticulate formulation of claim 1, wherein the surface potential of the lipid vesicles is from about +15 mV to about +40 mV at pH 7.4.

7. The nanoparticulate formulation of claim 1, wherein the PEGylated lipid is 1,2-distearoyl-sn-glycero-3-phosphoethanolamine-N-[amino(polyethylene glycol)] (DSPE-PEG).

8. The nanoparticulate formulation of claim 7, wherein the PEGylated lipid is DSPE-PEG2000.

9. The nanoparticulate formulation of claim 1, wherein the lipid vesicles comprise dipalmitoylphosphatidylcholine (DPPC) and cholesterol.

10. The nanoparticulate formulation of claim 9, wherein the DPPC:cholesterol molar ratio is from about 1 to 7 moles DPPC to about 1 to 4 moles cholesterol.

11. The nanoparticulate formulation of claim 1, wherein the lipid vesicles comprise DPPC, DOTAP, cholesterol, and DSPE-PEG2000.

12. The nanoparticulate formulation of claim 11, wherein the molar ratio of DPPC, DOTAP, cholesterol, and DSPE-PEG2000 is about 1 to 8 moles DPPC to about 0.05 to 1 mole DOTAP to about 0.5 to 2 moles cholesterol to about 0.1 to 5 moles DSPE-PEG2000.

13. A nanoparticulate formulation of an inhibitor of a poly (ADP-ribose) polymerase (PARP) enzyme, the formulation comprising a suspension of lipid vesicles in an aqueous medium, wherein the lipid vesicles have a positive surface charge, have an average diameter in the range from about 50 nm to about 200 nm, comprise a PARP inhibitor, and comprise a PEGylated lipid moiety;
wherein the lipid vesicles comprise DPPC, DOTAP, cholesterol, and DSPE-PEG2000; and
wherein the molar ratio of DPPC, DOTAP, cholesterol, and DSPE-PEG2000 is about 5.4 moles DPPC to about 0.25 moles DOTAP to about 0.78 moles cholesterol to about 0.14 moles DSPE-PEG2000; and wherein the PARP inhibitor is olaparib.

14. The nanoparticulate formulation of claim 12, wherein the molar ratio of DPPC, DOTAP, cholesterol, and DSPE-PEG2000 is about 1.4 moles DPPC to about 0.09 moles DOTAP to about 0.78 moles cholesterol to about 0.11 moles DSPE-PEG2000 and the PARP inhibitor is BMN-673.

15. The nanoparticulate formulation of claim 1, wherein the liposomes release the PARP inhibitor at a pH below 7.

16. The nanoparticulate formulation of claim 1 that is capable of selective delivery of the PARP inhibitor to tumor cells following intravenous injection of the formulation into a subject bearing a tumor.

17. The nanoparticulate formulation of claim 1, wherein the lipid vesicles further comprise a targeting moiety that binds to a tumor cell.

18. A kit comprising a PARP inhibitor formulation of claim 1, packaging materials, and instructions for administering the formulation to a subject having cancer, neurotrauma, or a neurodegenerative disease or condition.

* * * * *